US009833482B2

(12) United States Patent
Reisner et al.

(10) Patent No.: US 9,833,482 B2
(45) Date of Patent: Dec. 5, 2017

(54) MAMMALIAN FETAL PULMONARY CELLS AND THERAPEUTIC USE OF SAME

(71) Applicant: Yeda Research and Development Co. Ltd., Rehovot (IL)

(72) Inventors: Yair Reisner, Old Jaffa (IL); Elias Shezen, Rehovot (IL); Chava Rosen, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/363,814

(22) PCT Filed: Dec. 6, 2012

(86) PCT No.: PCT/IB2012/057042
§ 371 (c)(1),
(2) Date: Jun. 9, 2014

(87) PCT Pub. No.: WO2013/084190
PCT Pub. Date: Jun. 13, 2013

(65) Prior Publication Data
US 2014/0356335 A1  Dec. 4, 2014

Related U.S. Application Data

(60) Provisional application No. 61/568,240, filed on Dec. 8, 2011.

(51) Int. Cl.
*A61K 35/42* (2015.01)
*A61K 35/54* (2015.01)
*C12N 5/071* (2010.01)

(52) U.S. Cl.
CPC ............. *A61K 35/54* (2013.01); *A61K 35/42* (2013.01); *C12N 5/0688* (2013.01)

(58) Field of Classification Search
None
See application file for complete search history.

(56) References Cited

U.S. PATENT DOCUMENTS

| 2008/0112890 | A1  | 5/2008  | Lelkes et al. | |
|---|---|---|---|---|
| 2008/0274088 | A1* | 11/2008 | Panoskaltsis-Mortari | A61K 35/42 424/93.7 |
| 2013/0216508 | A1* | 8/2013  | Anversa | A61K 35/42 424/93.7 |

FOREIGN PATENT DOCUMENTS

| EP | 1099754 | 5/2001 |
|---|---|---|
| JP | 10-509034 | 9/1998 |
| JP | 2002-501513 | 1/2002 |
| JP | 2005-511501 | 4/2005 |
| JP | 2005-520513 | 7/2005 |
| RU | 2369634 | 10/2009 |
| WO | WO 96/14397 | 5/1996 |
| WO | WO 98/54301 | 12/1998 |
| WO | WO 03/022123 | 3/2003 |
| WO | WO 03/078588 | 9/2003 |
| WO | WO 2004/078022 | 9/2004 |
| WO | WO 2006/038211 | 4/2006 |
| WO | WO 2008/100555 | 8/2008 |
| WO | WO 2013/084190 | 6/2013 |
| WO | WO 2013/093920 | 6/2013 |
| WO | WO 2016/203477 | 12/2016 |

OTHER PUBLICATIONS

Provost et al, Early Human Development, 2010, vol. 86, p. 529-534.*
Supplementary Appendix to Kajstura et al, N Engl J Med, May 2011, vol. 364, 1795-1806 (76 pages).*
Robey, PG and Bianco, P, "Postnatal Stem CElls in Tissue Engineering." Principles in Tissue Engineering. Ed. Lanza,Langer and Vacanti. London: Academic Press, 2014 ($4^{th}$ Ed). pp. 645-646. Print.*
Fischer et al, "Pulmonary Passage is a major obstacle for intravenous stem cell delivery: The pulmonary first-pass effect" Stem Cells and Dev, 2009, vol. 18, No. 5, pp. 683-691.*
Written Opinion dated Jan. 13, 2016 From the Intellectual Property Office of Singapore Re. Application No. 11201402902V.
Search Report and Written Opinion dated Nov. 25, 2014 From the Intellectual Property Office of Singapore Re. Application No. 11201402902V.
Mondrinos et al. "A Tissue-Engineered Model of Fetal Distal Lung Tissue", American Journal of Physiology—Lung Cellular and Molecular Physiology, 293: L639-L650, First Published May 25, 2007. Discussion, Figs.2, 3, 6, 7.
International Preliminary Report on Patentability dated Jun. 19, 2014 From the International Bureau of WIPO Re. Application No. PCT/IB2012/057042.
International Search Report and the Written Opinion dated Apr. 5, 2013 From the International Searching Authority Re. Application No. PCT/IB2012/057042.
Adachi et al. "Treatment and Transfer of Emphysema by a New Bone Marrow Transplantation Method From Normal Mice to Tsk Mice and Vice Versa" Stem Cells, 24: 2071-2077, 2006.
Anversa et al. "Tissue-Specific Adult Stem Cells in the Human Lung", Nature Medicine, 17(9): 1038-1029, Sep. 2011.
Baber et al. "Intratracheal Mesenchymal Stein Cell Administration Attenuates Monocrotaline-Induced Pulmonary Hypertension and Endothelial Dysfunction", American Journal of Physiology: Heart and Circulatory Physiology, 292(2): H1120-H1128, Feb. 2007.
Cargnoni et al. "Transplantation of Allogeneic and Xenogeneic Placenta-Derived Cells Reduces Bleomycin-Induced Lung Fibrosis", Cell Transplantation, 18: 405-422, 2009.

(Continued)

*Primary Examiner* — Allison M Fox

(57) ABSTRACT

A pharmaceutical composition comprising as an active ingredient an isolated population of cell suspension from a mammalian fetal pulmonary tissue is disclosed. The fetal pulmonary tissue is at a developmental stage corresponding to that of a human pulmonary organ/tissue at a gestational stage selected from a range of about 20 to about 22 weeks of gestation. Methods of using the pharmaceutical composition are also disclosed.

24 Claims, 28 Drawing Sheets

(56) References Cited

OTHER PUBLICATIONS

Carraro et al. "Human Amniotic Fluid Stem Cells Can Integrate and Differentiate Into Epithelial Lung Lineages", Stem Cells, 26: 2902-2911, 2008.
Eventov-Friedman et al. "Embryonic Pig Liver, Pancreas, and Lung as a Source for Transplantation: Optimal Organogenesis Without Teratoma Depends on Distinct Time Windows", Proc. Natl. Acad. Sci. USA, PNAS, 102(8): 2928-2933, Feb. 22, 2005.
Kajstura et al. "Evidence for Human Lung Stem Cells", The New England Journal of Medicine, 364(19): 1795-1806, May 12, 2011.
Lee et al. "Allogeneic Human Mesenchymal Stem Cells for Treatment of E. coli Endotoxin-Induced Acute Lung Injury in the Ex Vivo Perfused Human Lung", Proc. Natl. Acad. Sci. USA, PNAS, 106(38): 16357-16362, Sep. 22, 2009.
Loi et al. "Limited Restoration of Cystic Fibrosis Lung Epithelium In Vivo With Adult Bone Marrow-Derived Cells", American Journal of Respiratory and Critical Care Medicine, 173: 171-179, 2006.
MacPherson et al. "Bone Marrow-Derived SP Cells Can Contribute to the Respiratory Tract of Mice In Vivo", Journal of Cell Science, 118: 2441-2450, 2005.
Moodley "Evidence for Human Lung Stem Cells", The New England Journal of Medicine, 365(5): 464-466, Aug. 4, 2011.
Moodley et al. "Human Amnion Epithelial Cell Transplantation Abrogates Lung Fibrosis and Augments Repair", American Journal of Respiratory and Critical Care Medicine, 182: 643-651, Jun. 3, 2010.
Moodley et al. "Human Umbilical Cord Mesenchymal Stem Cells Reduce Fibrosis of Bleomycin-Induced Lung Injury", The American Journal of Pathology, 175(1): 303-313, Jul. 2009.
Sakagami et al. "Patient-Derived GM-CSF Autoantibodies Reproduce Pulmonary Alveolar Proteinosis in Nonhuman Primates", Online Supplement, American Journal of Respiratory and Critical Care Medicine, p. 1-23, 2010.
Sakagami et al. "Patient-Derived Granulocyte/Macrophage Colony-Stimulating Factor Autoantibodies Reproduce Pulmonary Alveolar Proteinosis in Nonhuman Primates", American Journal of Respiratory and Critical Care Medicine, 182: 49-61, Mar. 11, 2010.
Sueblinvong et al. "Stem Cells and Cell Therapy Approaches in Lung Biology and Diseases", Translational Research, 156(3): 188-205, 2010.
Suzuki et al. "Heredity Pulmonary Alveolar Proteinosis. Pathogenesis, Presentation, Diagnosis, and Therapy", American Journal of Respiratory and Critical Care Medicine, 182: 1292-1304, Jul. 29, 2010.
Weiss "Stem Cells and Cell Therapies for Cystic Fibrosis and Other Lung Diseases", Pulmonary Pharmacology & Therapeutics, 21: 588-594, 2008.
Weiss et al. "Stem Cells and Cell Therapies in Lung Biology and Lung Diseases", Proceedings of the American Thoracic Society, 5(5): 637-667, Jul. 15, 2008.
Wong et al. "Identification of a Bone Marrow-Derived Epithelial-Like Population Capable of Repopulating Injured Mouse Airway Epithelium", The Journal of Clinical Investigation, 119(2): 336-348, Feb. 2009.
European Search Report and the European Search Opinion dated May 11, 2016 From the European Patent Office Re. Application No. 16151376.7.
Examination Report dated Oct. 5, 2016 From the Intellectual Property Office of Singapore Re. Application No. 11201402902V.
International Search Report and the Written Opinion dated Sep. 12, 2016 From the International Searching Authority Re. Application No. PCT/IL2016/050638.
Rosen et al. "Preconditioning Allows Engraftment of Mouse and Human Embryonic Lung Cells, Enabling Lung Repair in Mice", Nature Medicine, 21(8): 869-879, Published Online Jul. 13, 2015.
Summer et al. "Embryonic Lung Side Population Cells Are Hematopoietic and Vascular Precursors", American Journal of Respiratory Cell and Molecular Biology, 33: 32-40, 2005.
Notice of Reason for Rejection dated Sep. 30, 2016 From the Japan Patent Office Re. Application No. 2014-545442 and Its Translation Into English.
Schlichenmaier et al. "Expression of Cytokeratin 18 During Pre- and Post-Natal Porcine Lung Development", Anatomia, Histologia, Embryologia 31(5): 273-277, Oct. 2002.
Request for Substantive Examination dated Nov. 18, 2016 From the ROSPATENT, Federal Government Institution, Federal Institute of Industrial Property of the Federal Service of Intellectual Property, Patents and Trademarks of the Russian Federation Re. Application No. 2014127338 and Its Translation Into English. (11 Pages).
Notification of Office Action and Search Report dated Feb. 13, 2017 From the State Intellectual Property Office of the People's Republic of China Re. Application No. 201280069291.9. (11 Pages).
Translation of Notification of Office Action and Search Report dated Feb. 13, 2017 From the State Intellectual Property Office of the People's Republic of China Re. Application No. 201280069291.9. (17 Pages).
Notice of Reason for Rejection dated Apr. 25, 2017 From the Japan Patent Office Re. Application No. 2014-545442 and Its Translation Into English. (9 Pages).

\* cited by examiner

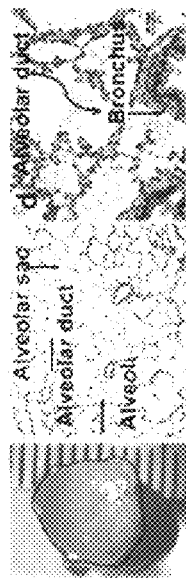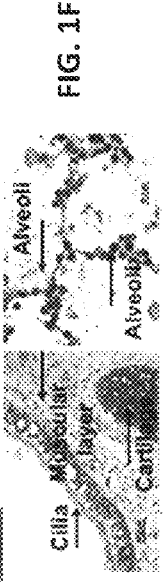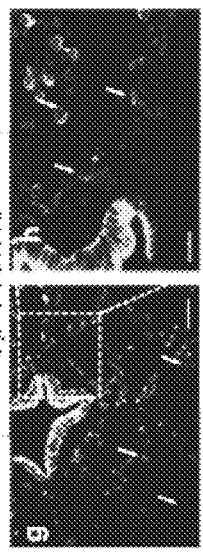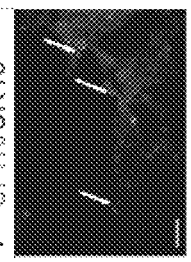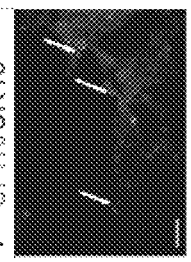

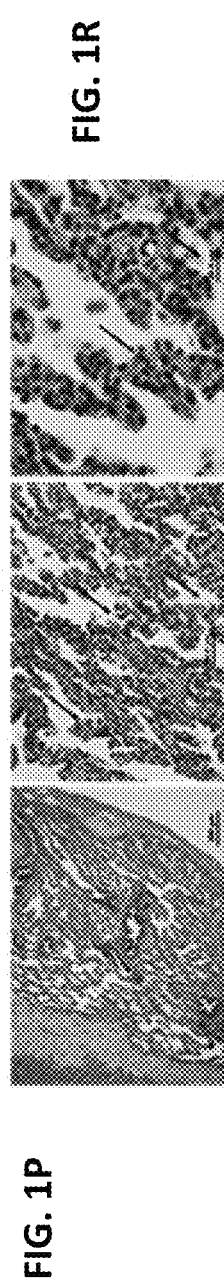

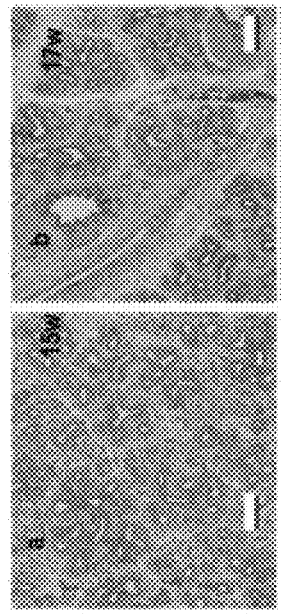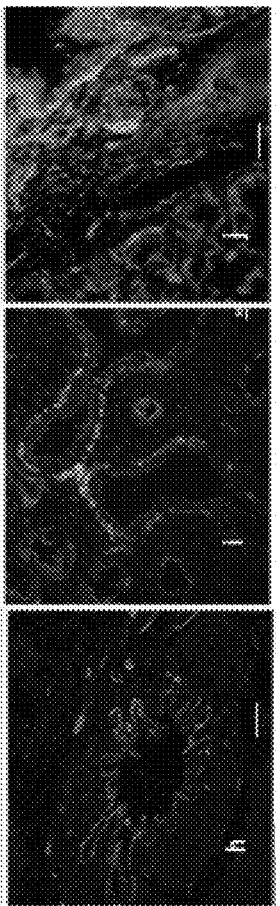

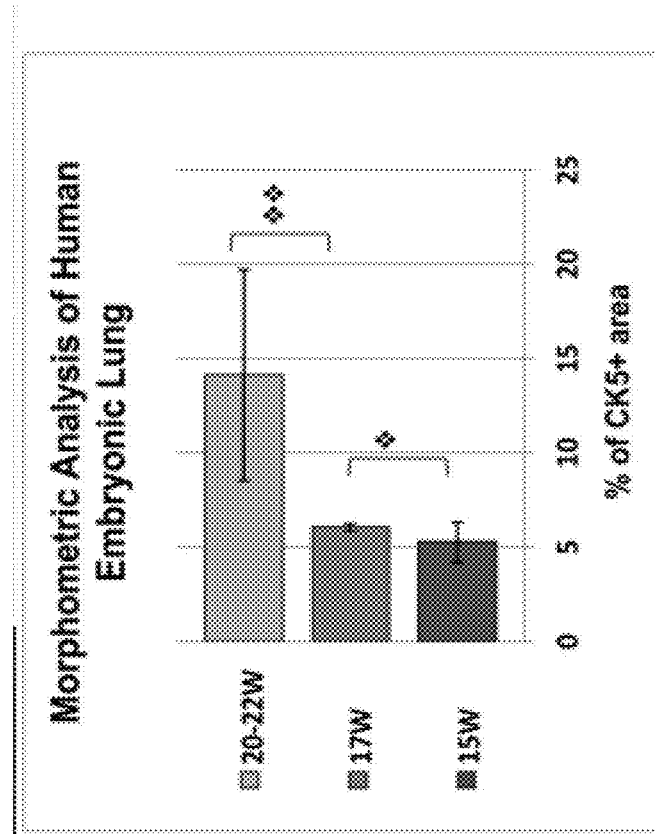
FIG. 2O
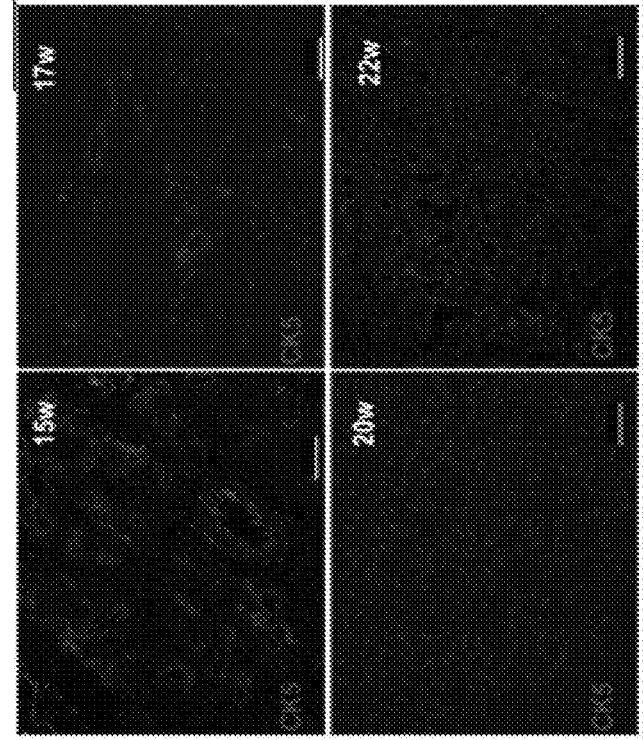
FIG. 2K FIG. 2L
FIG. 2M FIG. 2N

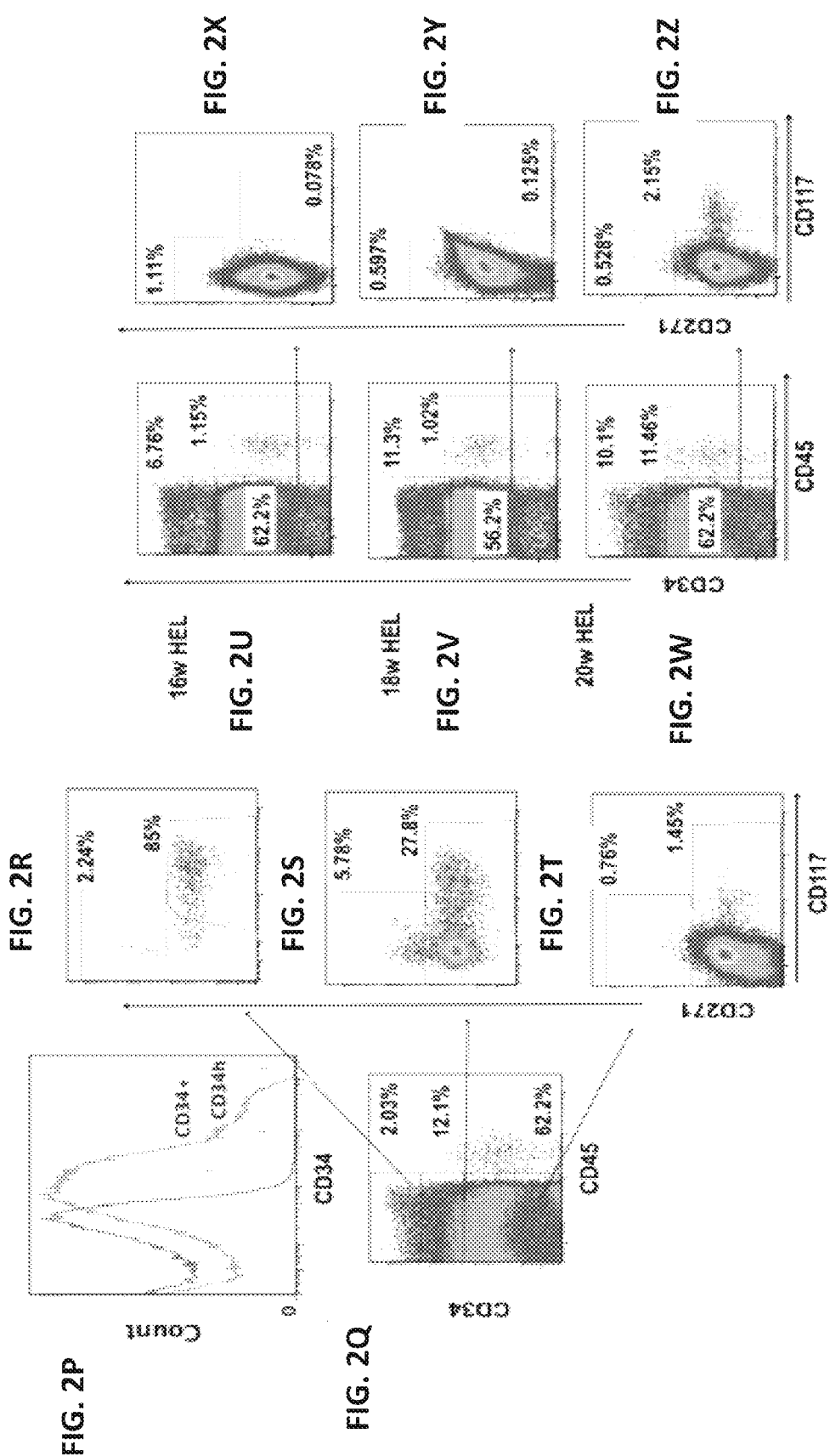

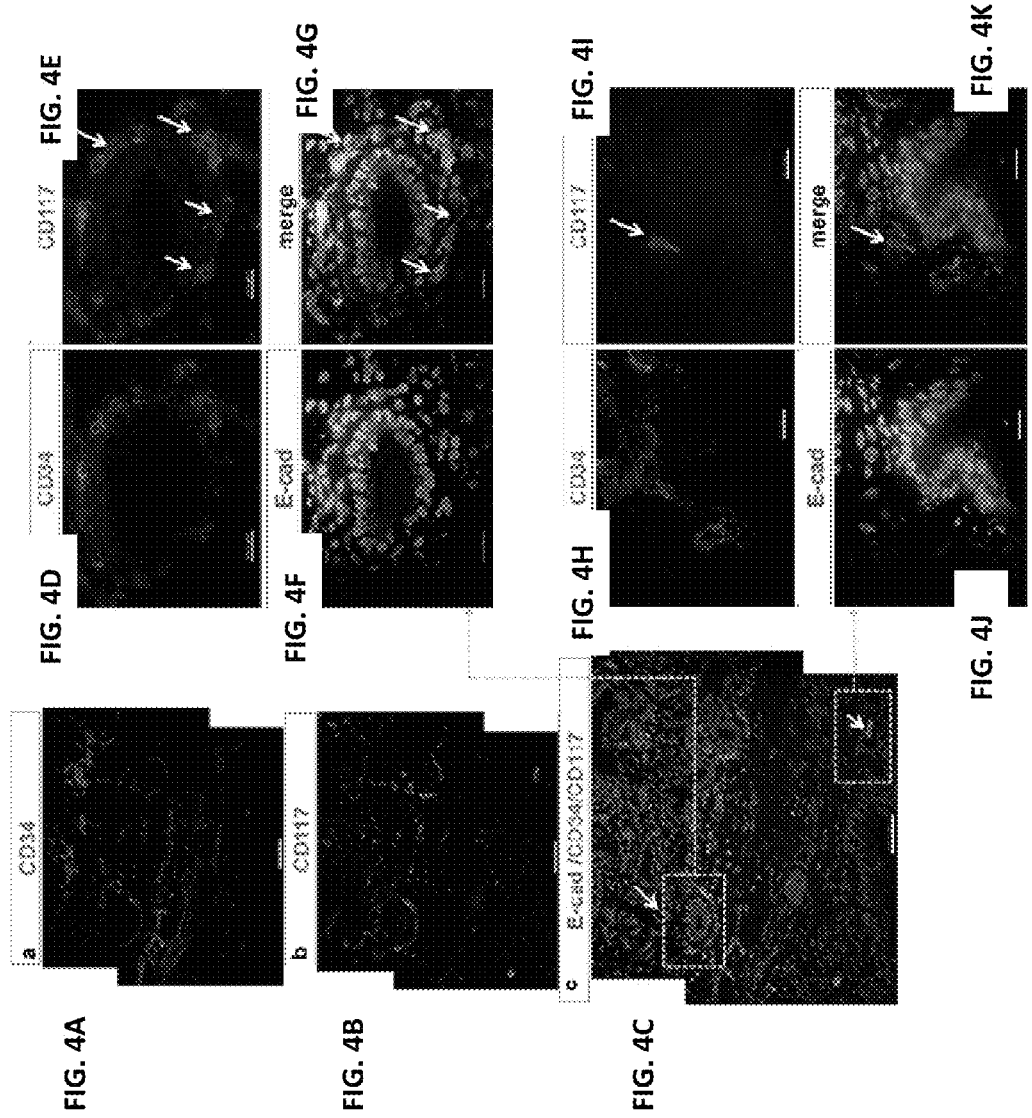

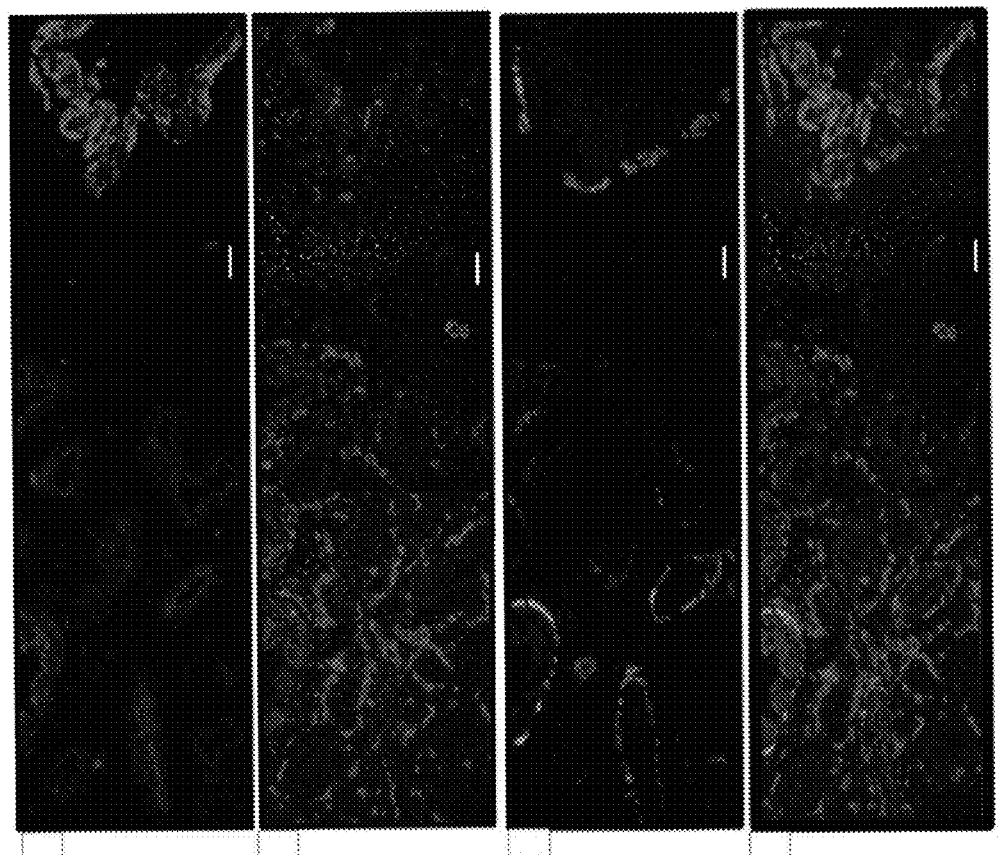

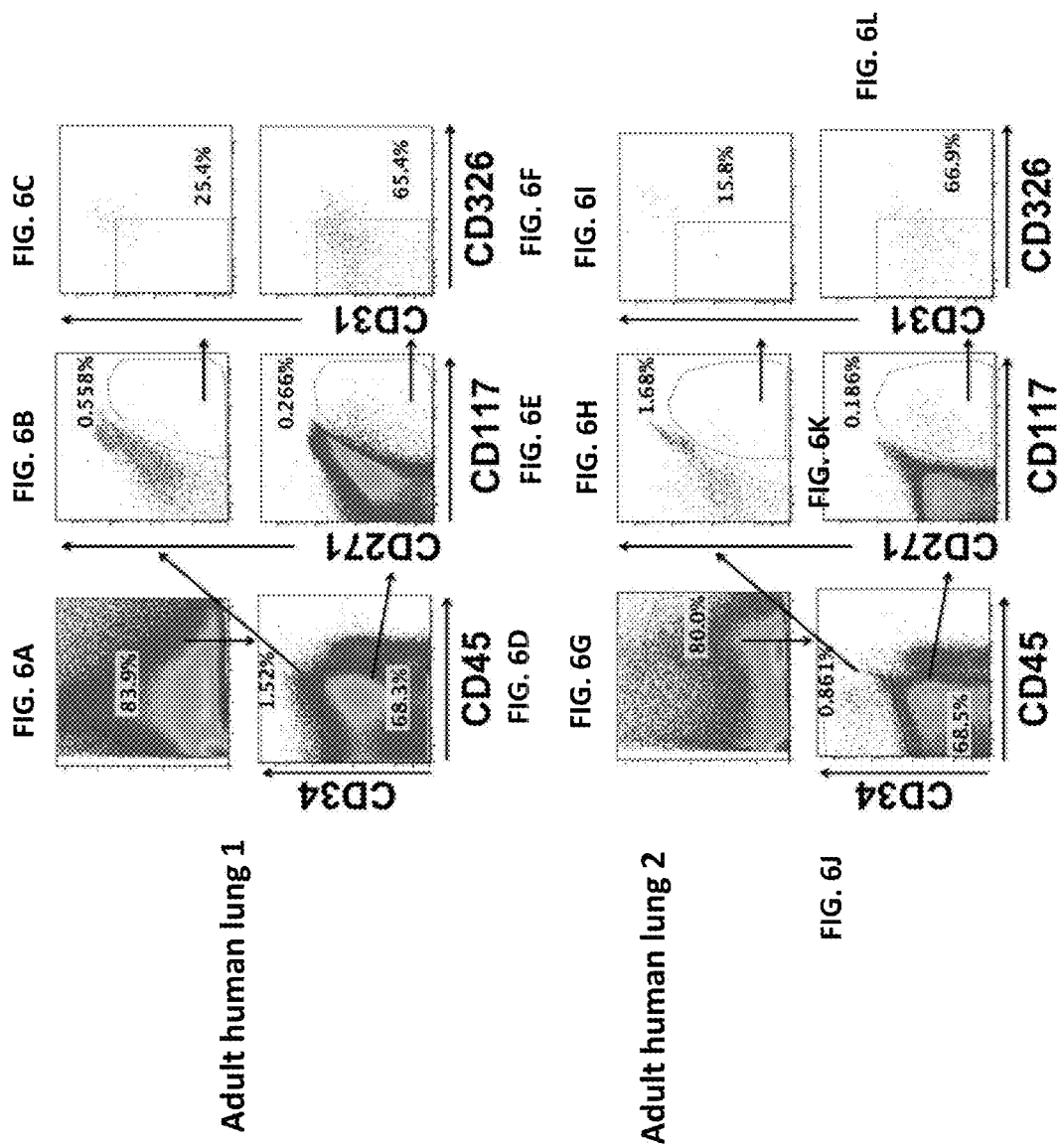

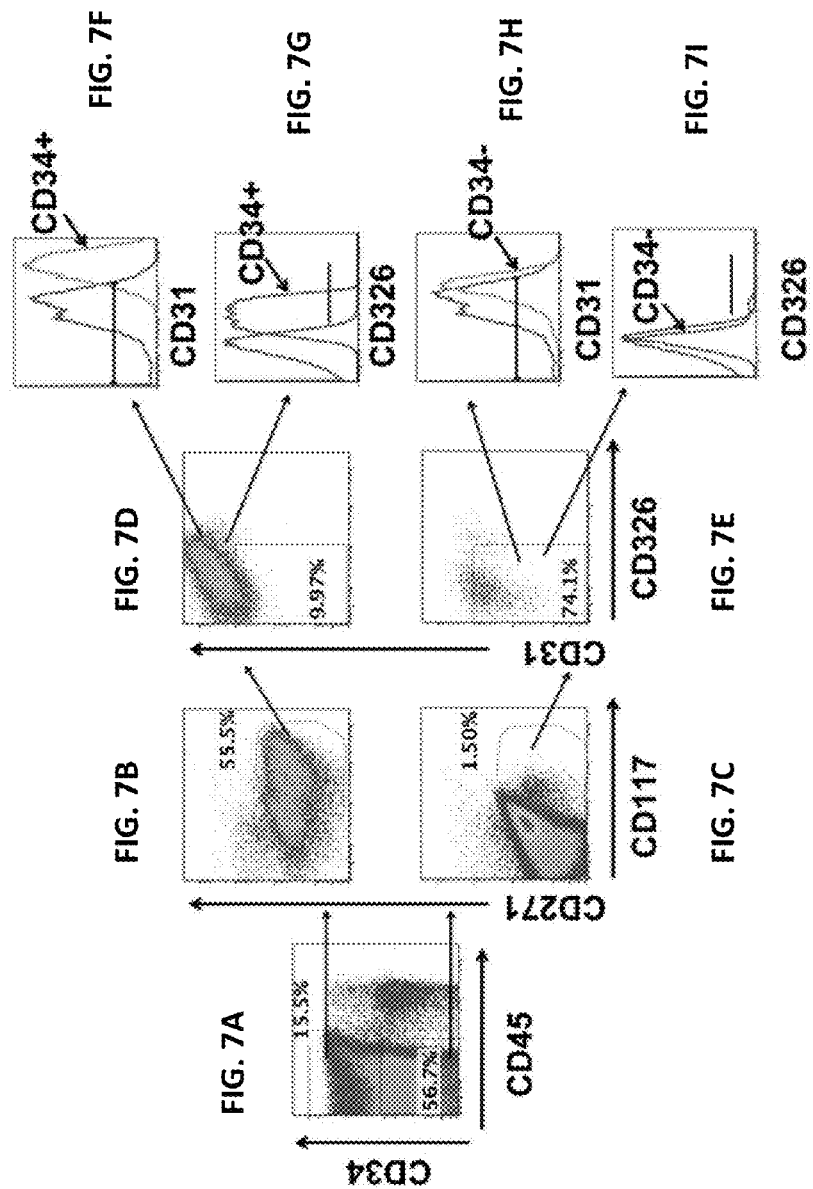

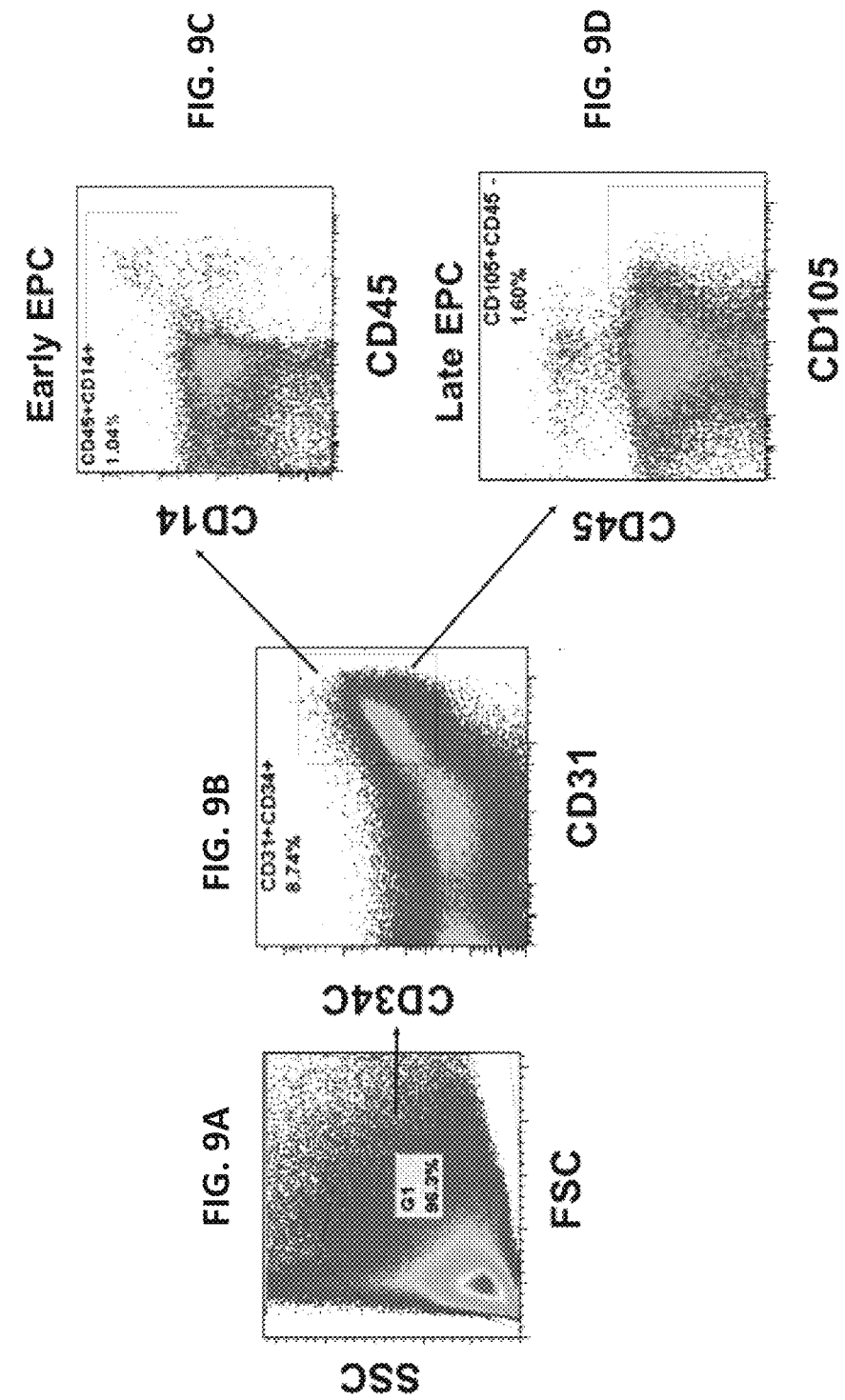

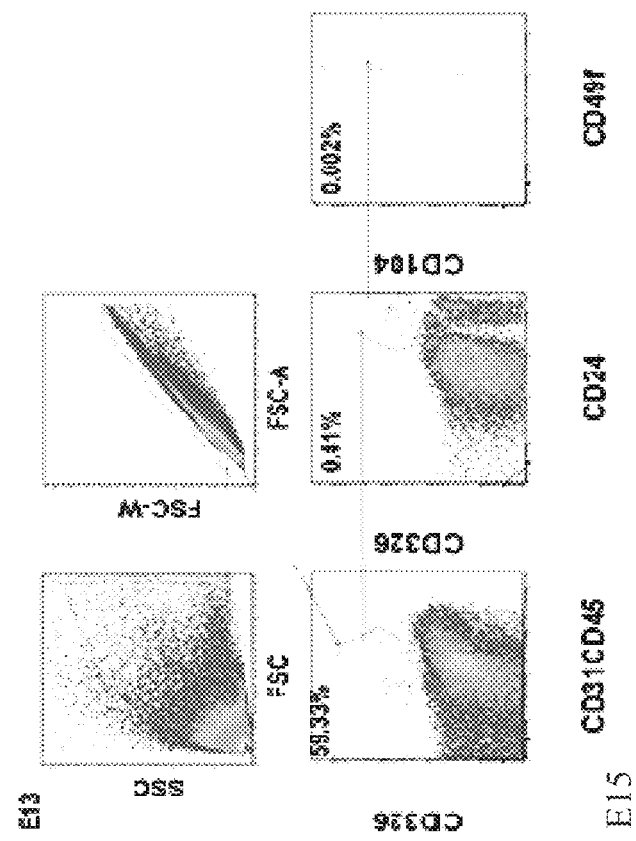
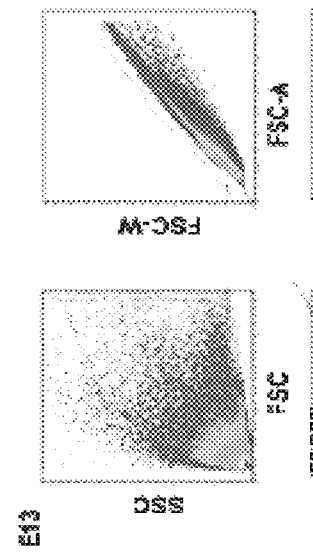
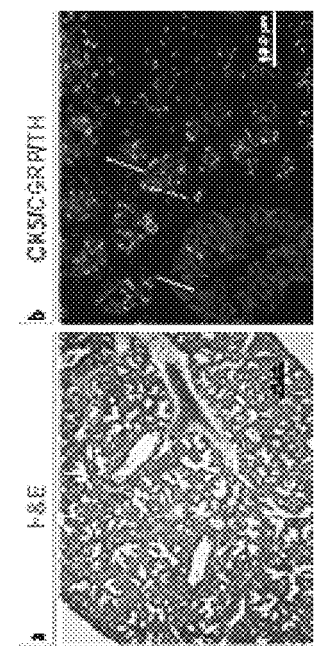
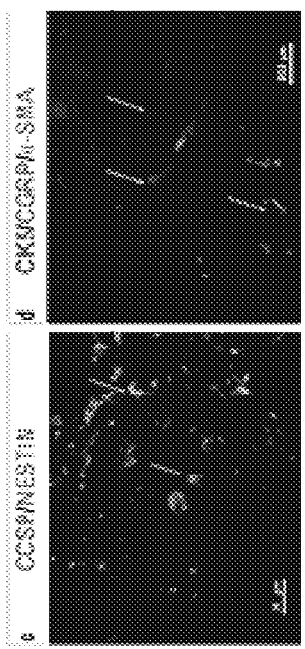
FIG. 11A  FIG. 11B  FIG. 11C  FIG. 11D
FIG. 11E  FIG. 11F  FIG. 11G  FIG. 11H  FIG. 11I

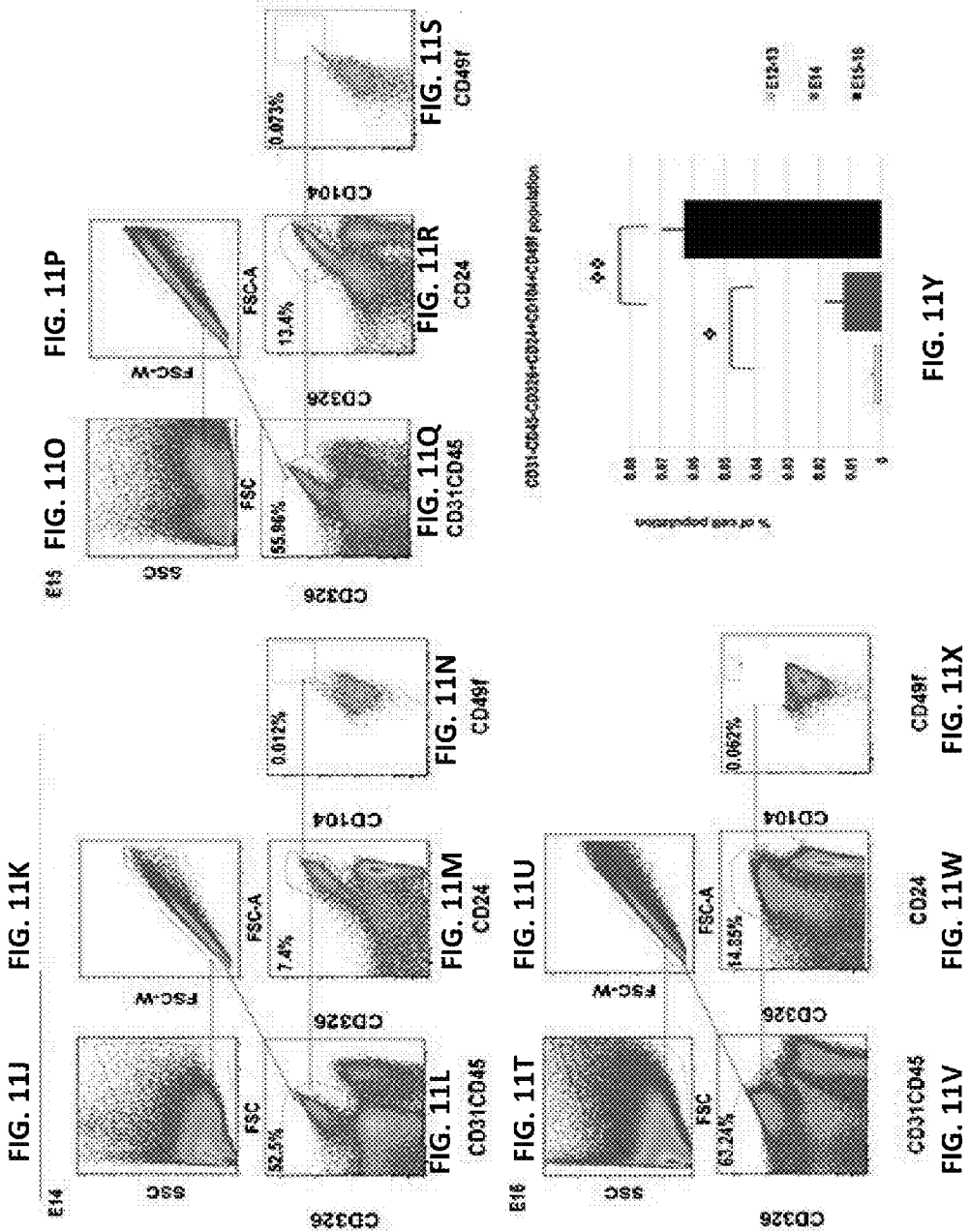

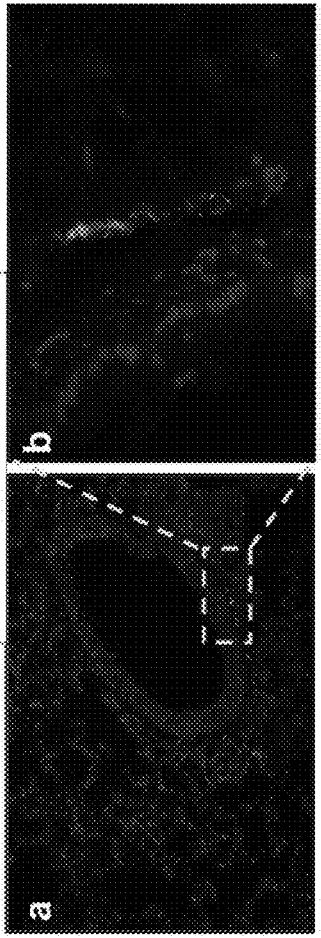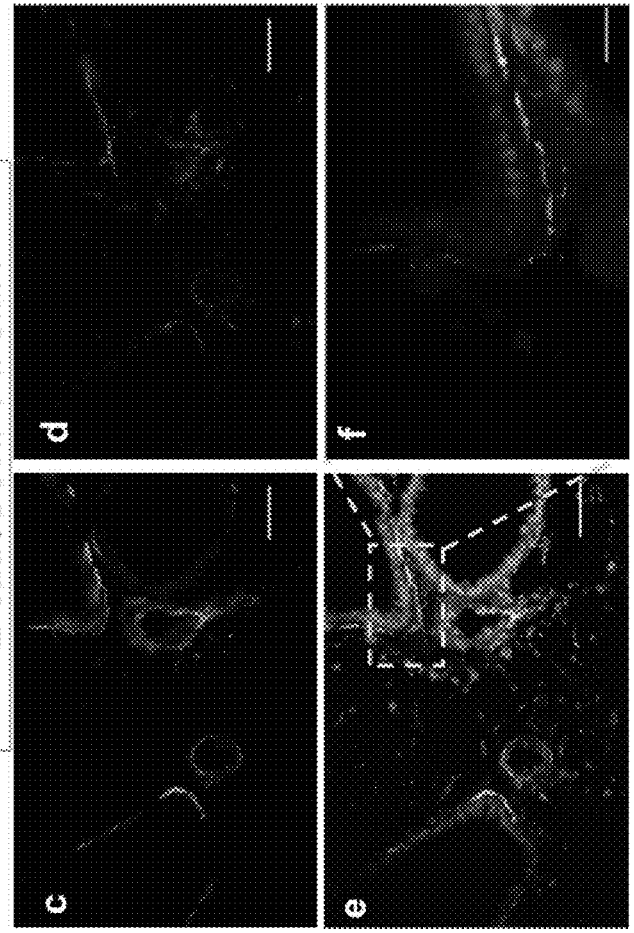

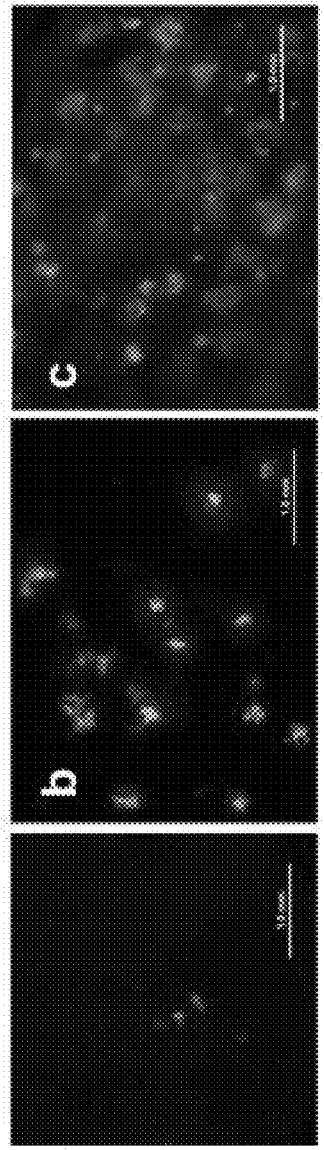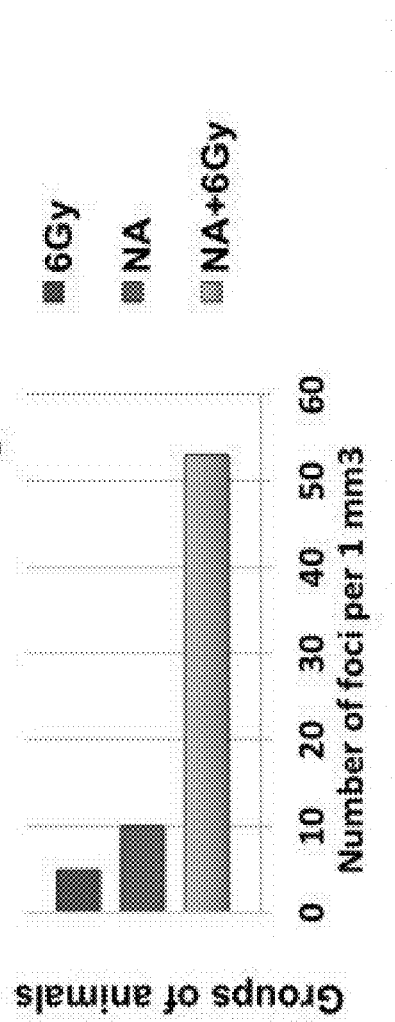
FIG. 13A  FIG. 13B  FIG. 13C  FIG. 13D

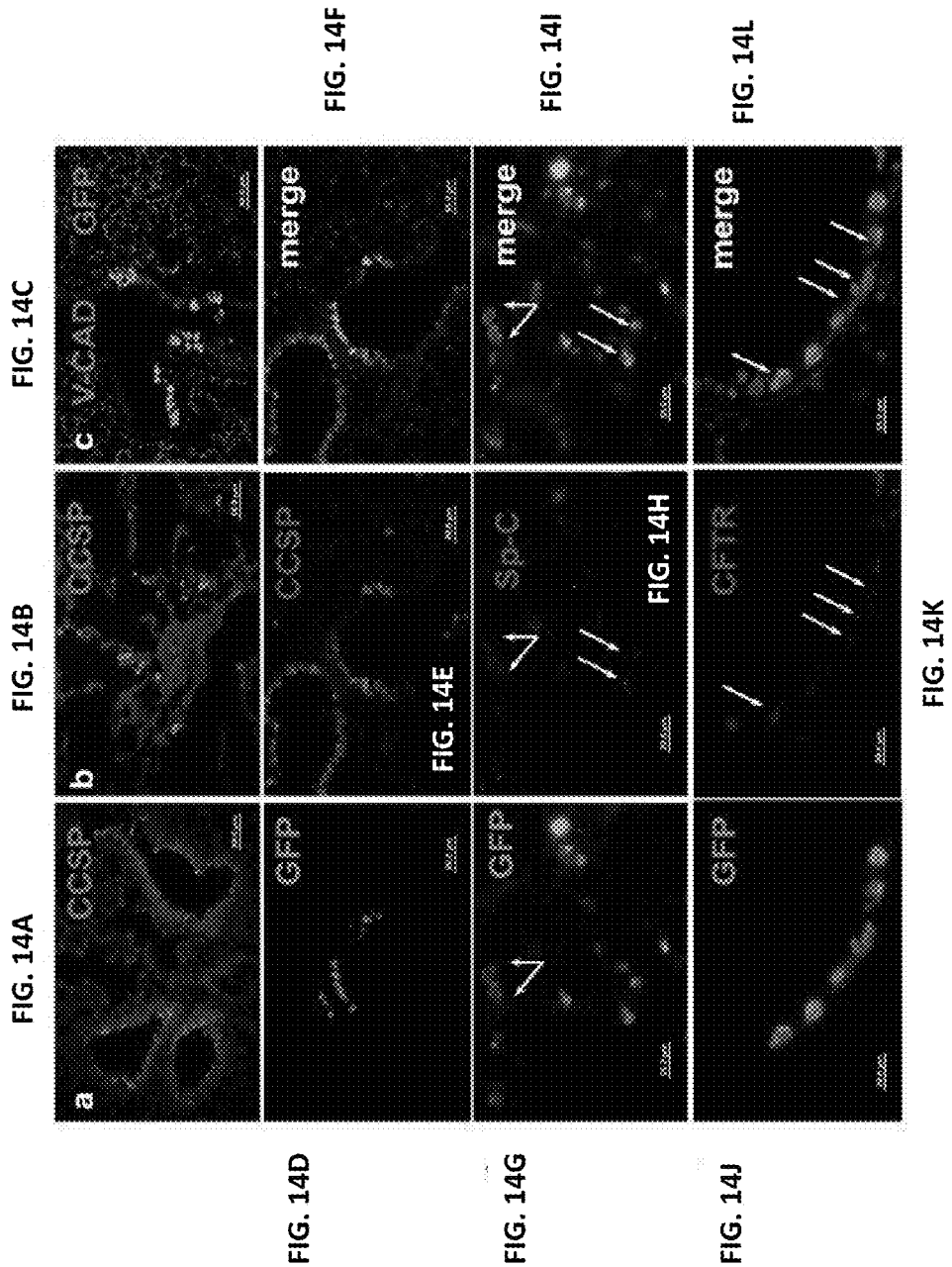

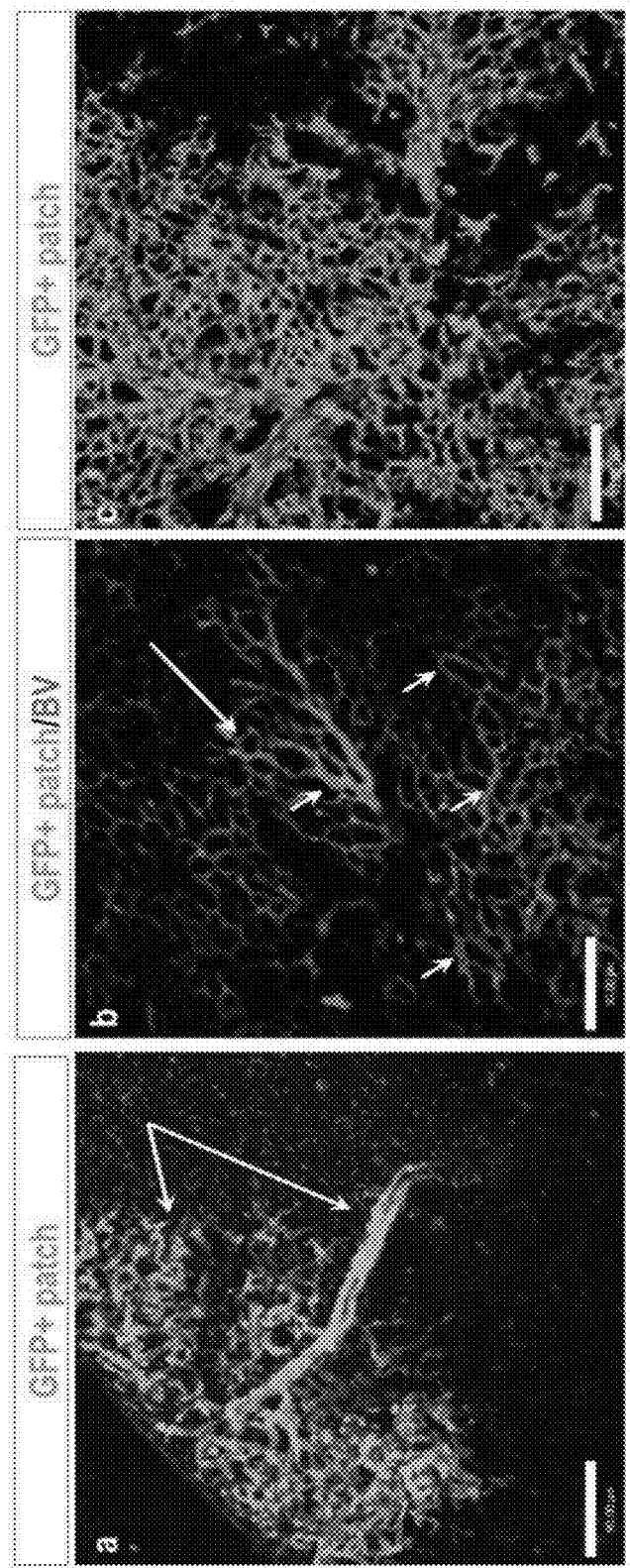

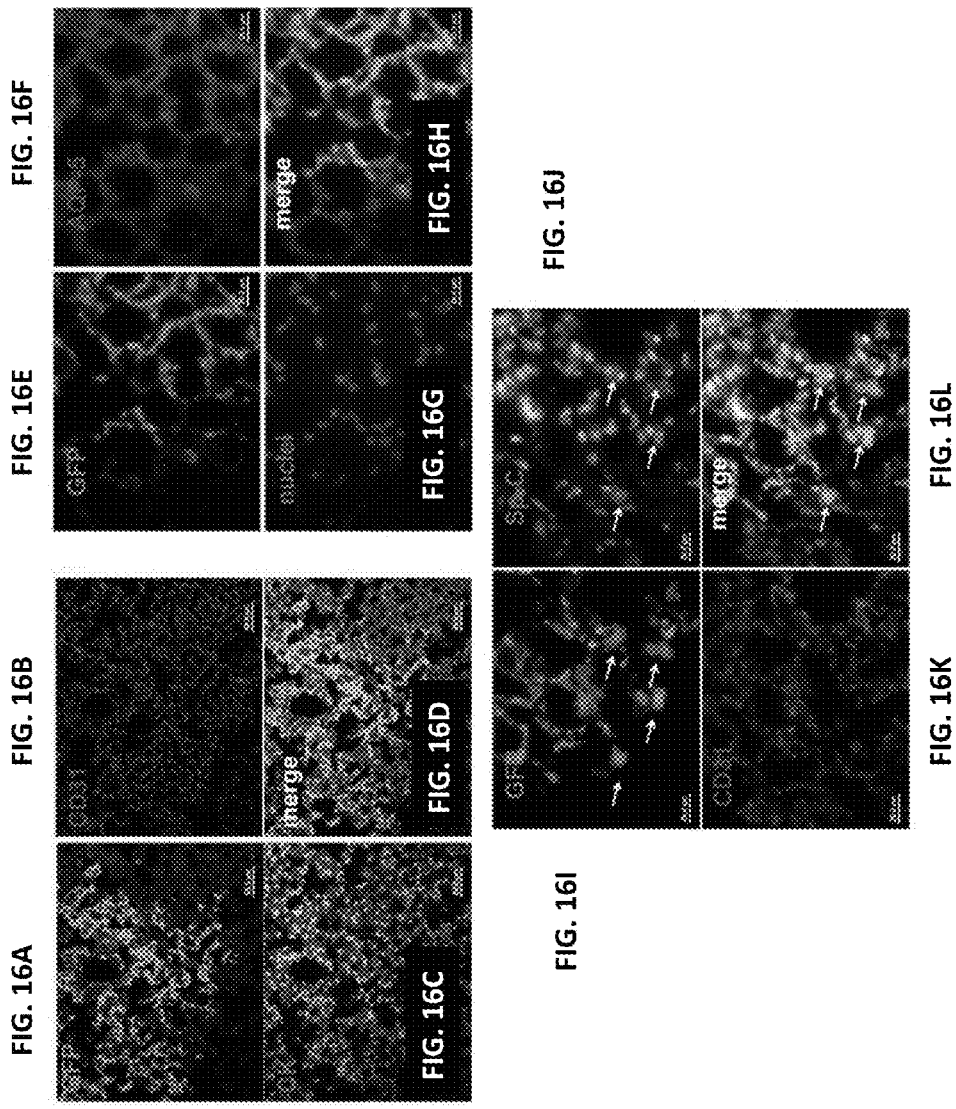

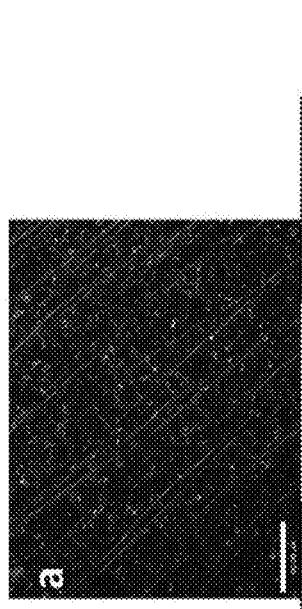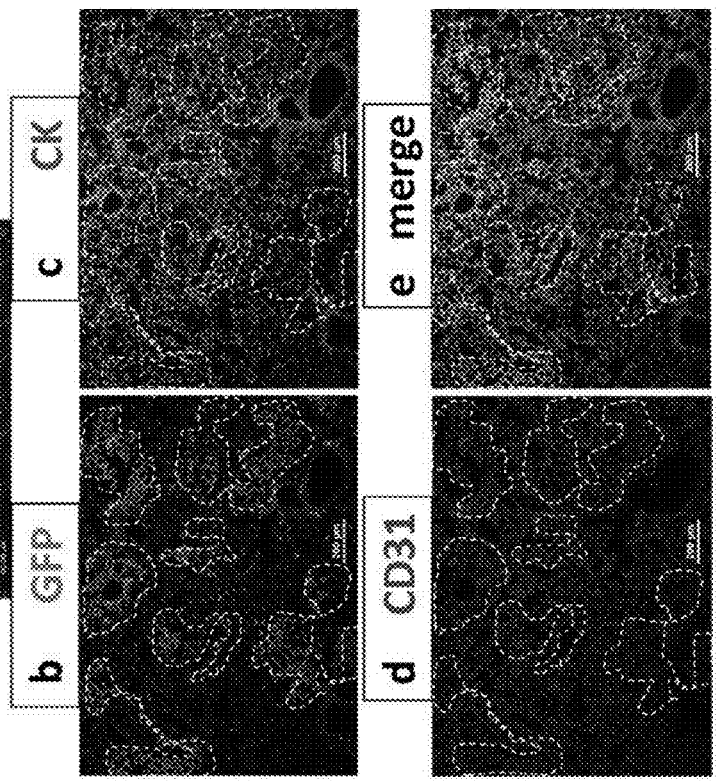
FIG. 17A
FIG. 17B
FIG. 17C
FIG. 17D
FIG. 17E

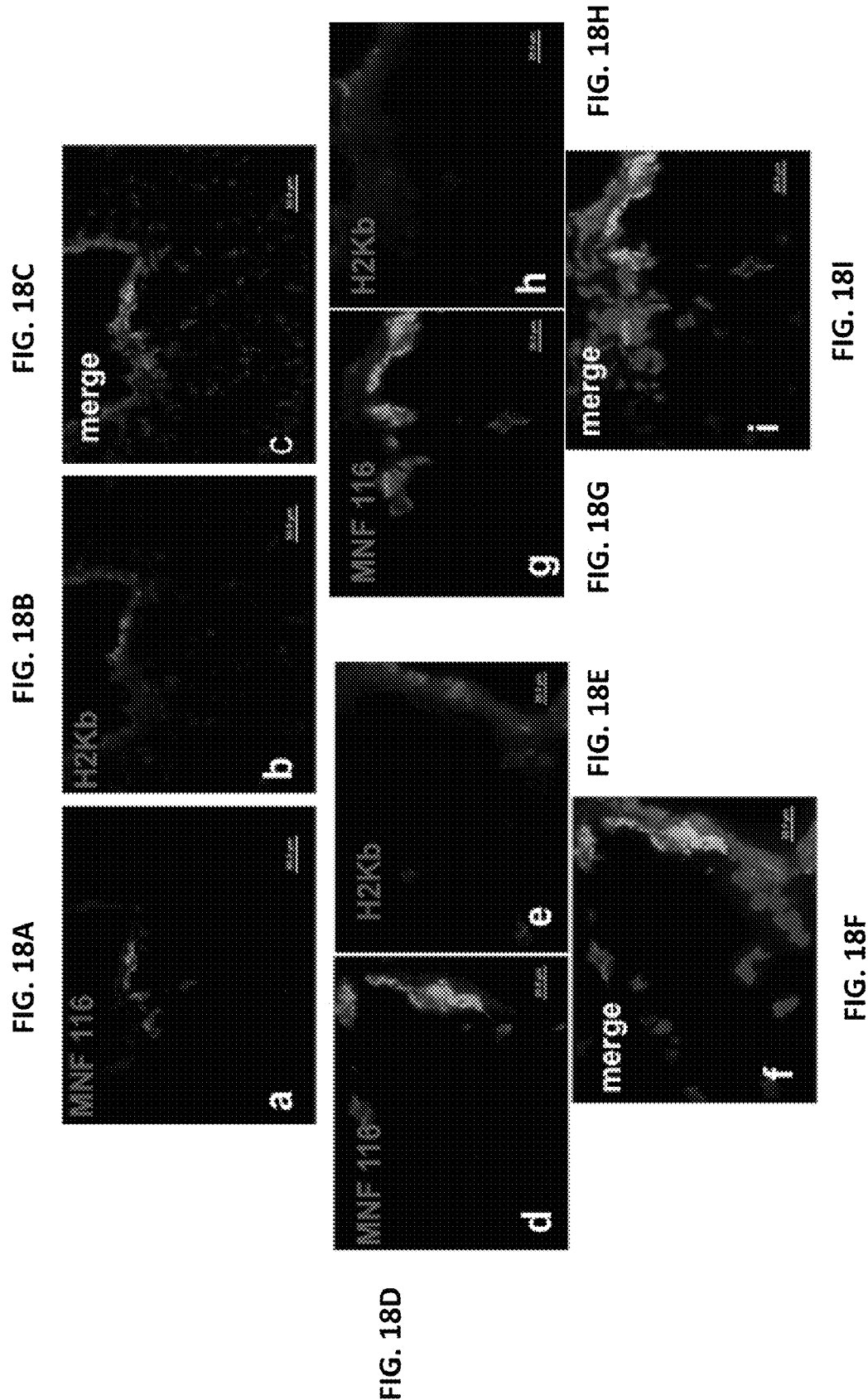

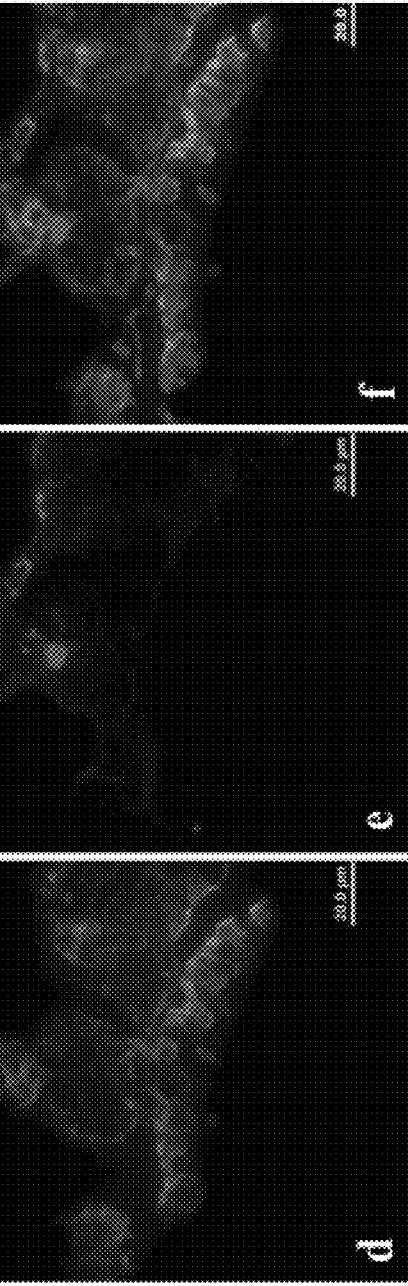

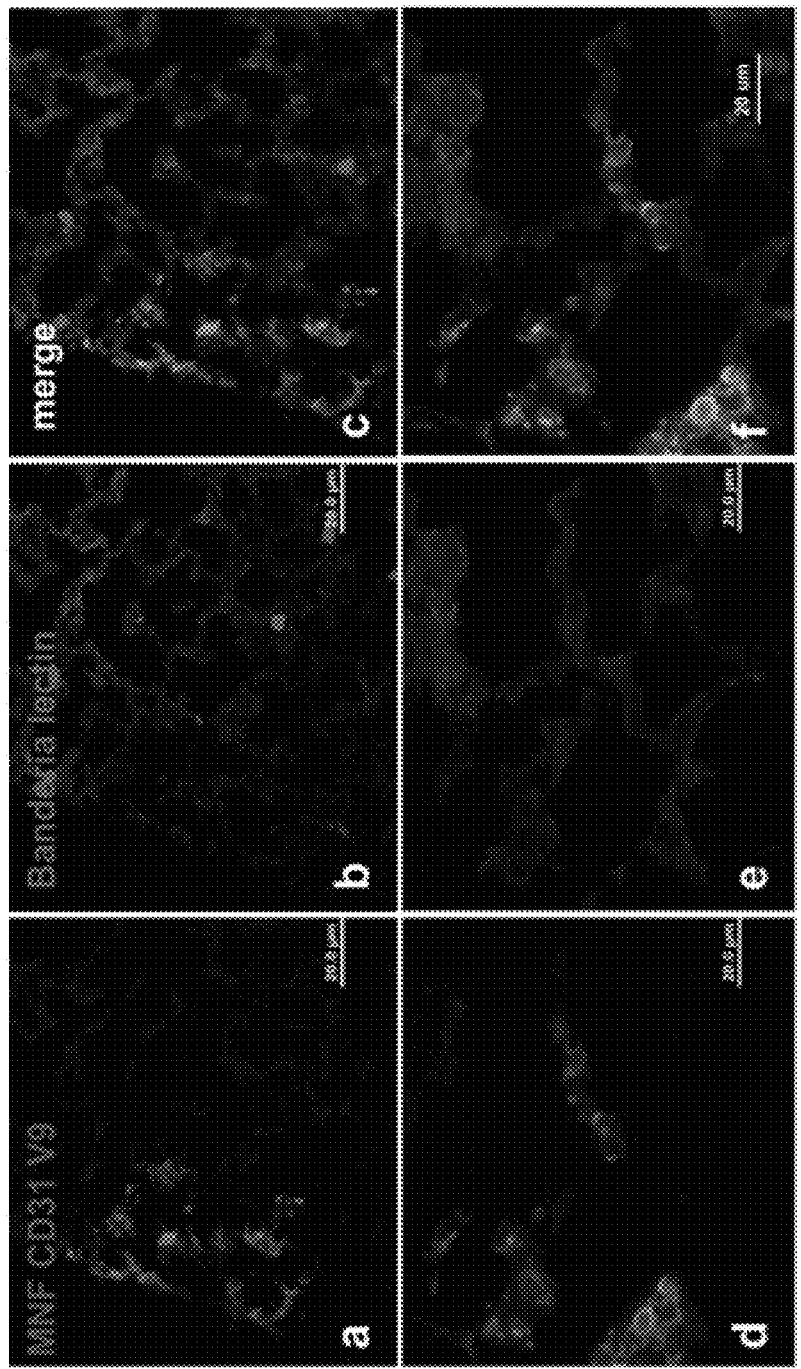

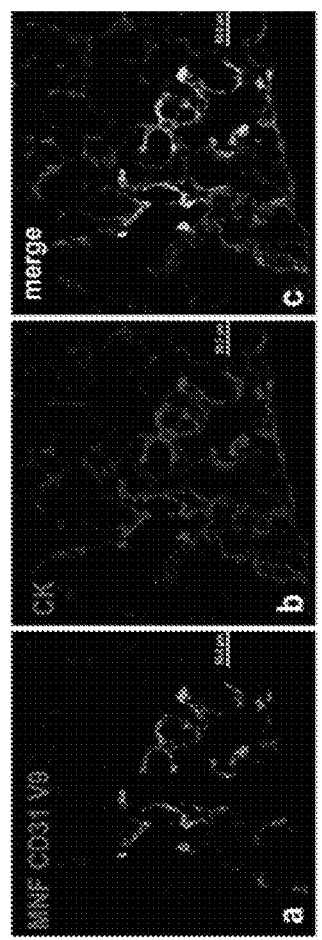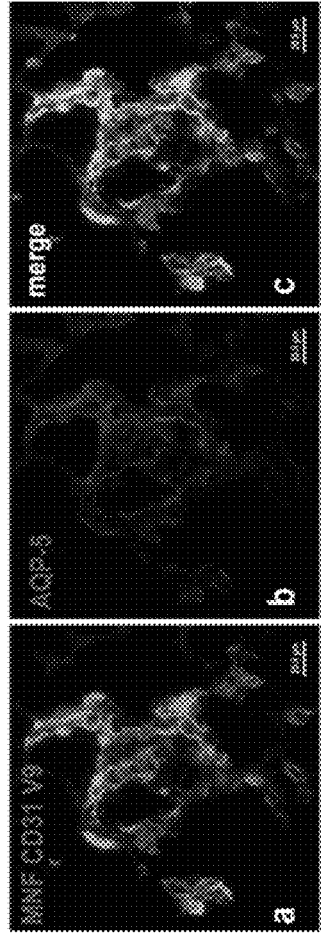

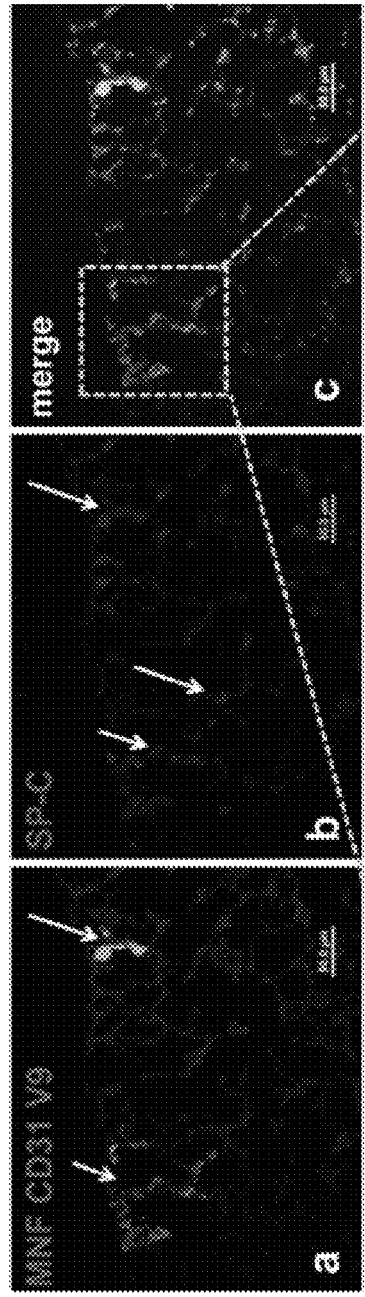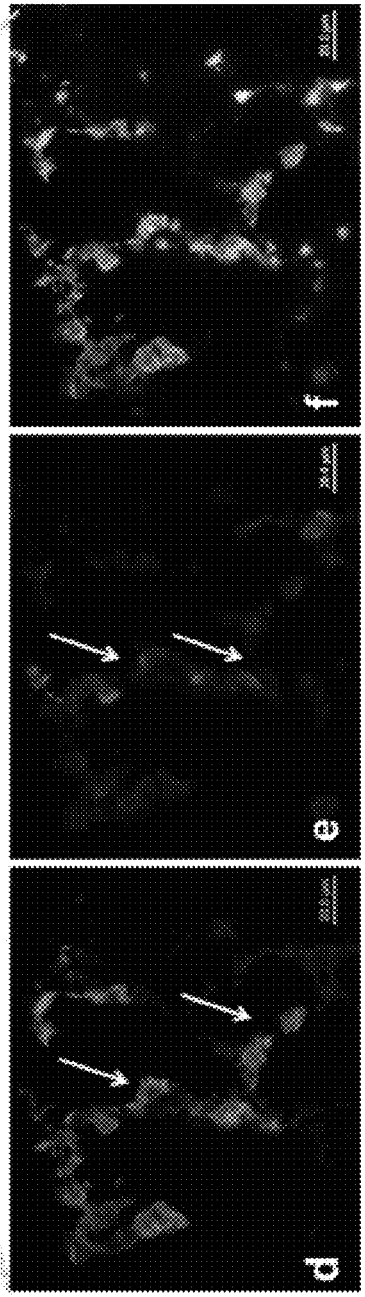

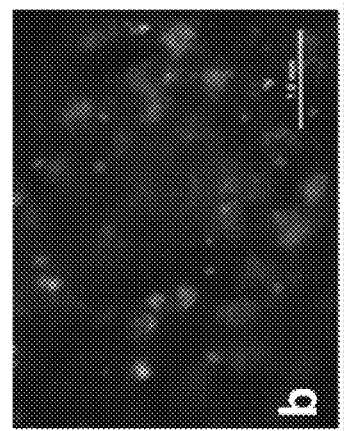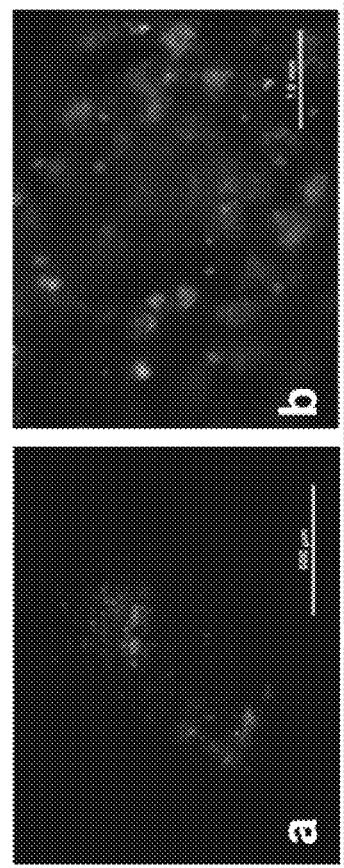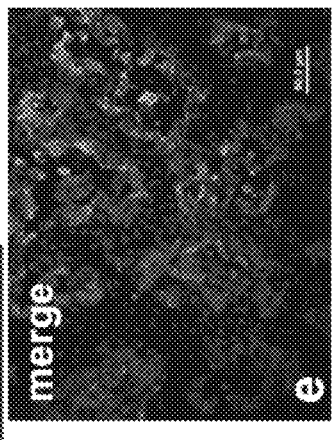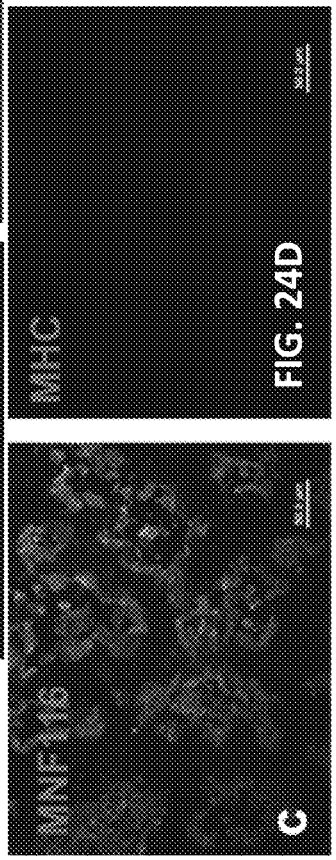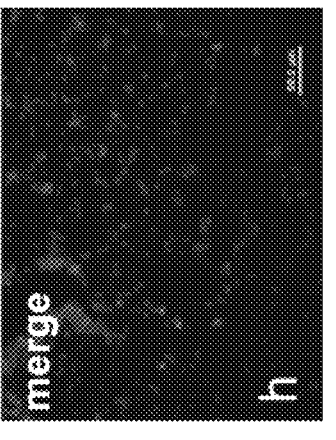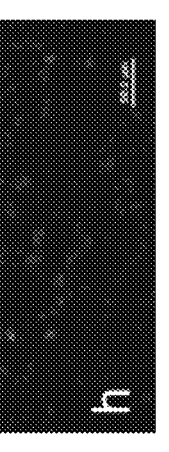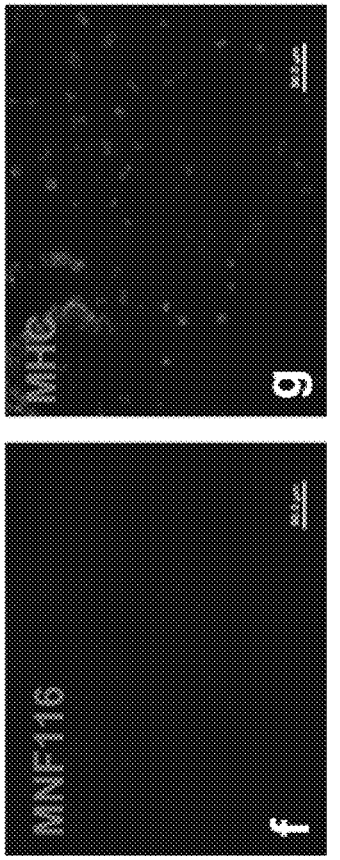
FIG. 24A  FIG. 24B  FIG. 24C  FIG. 24D  FIG. 24E  FIG. 24F  FIG. 24G  FIG. 24H

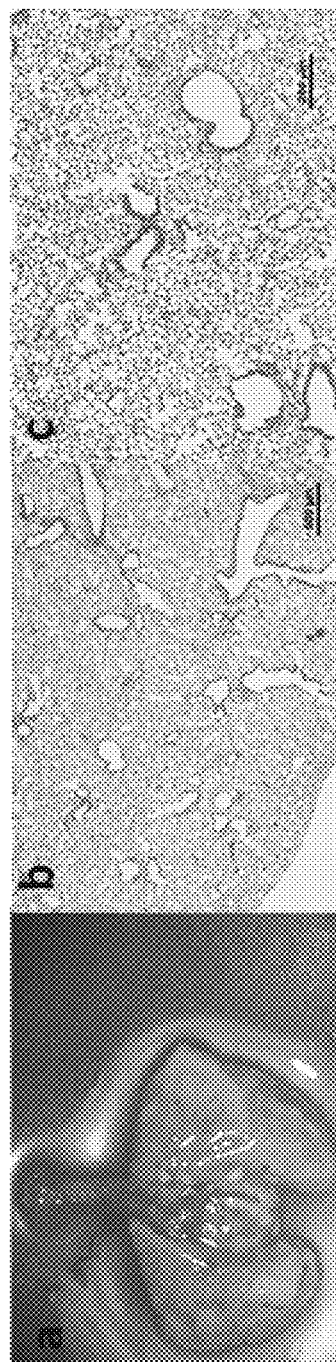
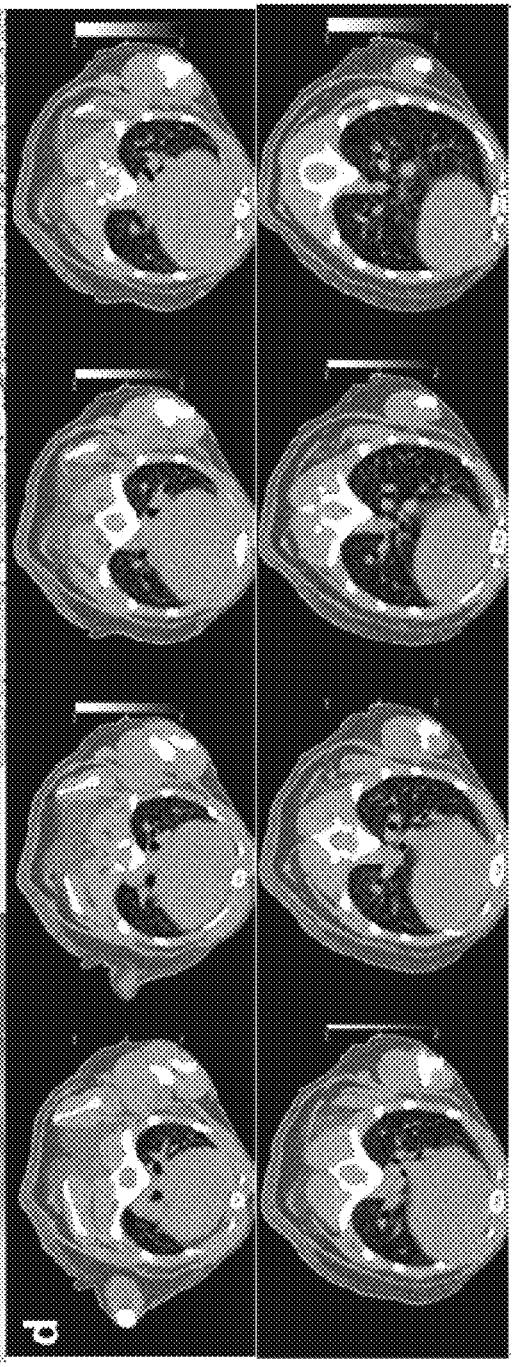
FIG. 25A  FIG. 25B  FIG. 25C  FIG. 25D

MAMMALIAN FETAL PULMONARY CELLS AND THERAPEUTIC USE OF SAME

FIELD AND BACKGROUND OF THE INVENTION

The present invention, in some embodiments thereof, relates to mammalian embryonic pulmonary cells and, more particularly, but not exclusively, to the use of same for therapeutic applications.

Respiratory diseases are a major cause of mortality and morbidity, ranked by the world health organization as second most in incidence, prevalence, morbidity, mortality and cost. Most currently available therapies only slightly improve the quality of life of lung disease patients, and do not prevent the loss of gas-exchange surface, which is a major consequence of progression in a variety of pulmonary pathologies. Thus, currently, the only definitive treatment for end-stage lung disease is the replacement of the damaged organ, but many patients die while on the waiting list due to a severe shortage of organs for transplantation.

Previous studies defined "optimal windows" for transplantation of human and pig embryonic precursors of different organs. These "optimal windows" for transplantation were defined by three parameters: lack of risk for teratoma, functional properties of the growing tissue, as well as low immunogenicity. For example, implantation into SCID mice of different pig embryonic precursor tissues, revealed distinct time 'windows' during which the tissue exhibits properties suitable for transplantation, with kidney and liver exhibiting optimal properties at 28 days while the lung 'window' was shown to occur much later, at 56 days, of porcine gestational age [Eventov-Friedman S. et al., Proc Nat Acad of Sciences. (2005) 102(8): 2928]. Studies using pig pancreatic precursor tissue suggested its optimum at 42 days, at which time this tissue demonstrates marked ability to correct streptozotocin-induced hyperglycemia in immunosuppressed mice, and more recently, in non-human primates. Moreover, recent studies have shown that transplantation of pig embryonic spleen tissues, harvested at specific gestational time points, are able to correct hemophilia in FVIII deficient mice.

During the past decade, the potential curative role of stem cell based therapies has been extensively investigated. Recent findings suggest that early progenitors derived from adult tissues, such as the bone marrow or from the umbilical cord blood, amniotic fluid or placenta, including mesenchymal stem cells, endothelial progenitors or circulating fibrocytes and a variety of other populations, could structurally engraft and differentiate as airways and alveolar epithelial cells or as vascular endothelial or interstitial lung cells and could be utilized in repair and regeneration of injured or diseased lungs [Baber S R et al., American Journal of Physiology-Heart and Circulatory Physiology. (2007) 292 (2): H1120; Weiss D J. Pulm Pharmacol Ther. (2008) 21(4):588-94; Weiss D J et al., Proceedings of the American thoracic society: Am Thoracic Soc; (2008) p. 637; Sueblinvong V and Weiss D J. Translational Research. (2010) 156(3): 188-205]. However, lack of significant epithelial transdifferentiation, the extremely complex structure of the lung, comprised of more than 40 different cell types, and a low engraftment rate of transplanted cells in the lung, in different experimental models, represent a major challenge.

Additional background art includes:

PCT Publication No. WO 2006/038211 relates to methods of providing a pancreatic, lymphoid/hematopoietic or pulmonary organ and/or tissue function to a mammalian subject. The method comprising transplanting into the subject a developing mammalian pancreatic, lymphoid/hematopoietic or pulmonary organ/tissue graft, respectively. The pulmonary graft disclosed in WO 2006/038211 is at a developmental stage essentially corresponding to that of a porcine pulmonary organ/tissue at a gestational stage selected from a range of about 42 to about 80 days of gestation.

PCT Publication No. WO 2004/078022 relates to methods of treating a disorder associated with pathological organ or tissue physiology or morphology. The method is effected by transplanting into a subject a mammalian organ or tissue graft (e.g. renal, pancreatic, hepatic, cardiac or lymphoid organ or tissue graft) selected not substantially expressing or presenting at least one molecule capable of stimulating or enhancing an immune response in the subject.

SUMMARY OF THE INVENTION

According to an aspect of some embodiments of the present invention there is provided a pharmaceutical composition comprising as an active ingredient an isolated population of cell suspension from a mammalian fetal pulmonary tissue, wherein the fetal pulmonary tissue is at a developmental stage corresponding to that of a human pulmonary organ/tissue at a gestational stage selected from a range of about 20 to about 22 weeks of gestation.

According to an aspect of some embodiments of the present invention there is provided a method of regenerating an epithelial, mesenchymal and/or endothelial tissue in a subject in need thereof, the method comprising administering to the subject a therapeutically effective amount of the pharmaceutical composition of some embodiments of the present invention, thereby regenerating the epithelial, mesenchymal and/or endothelial tissue.

According to an aspect of some embodiments of the present invention there is provided a method of treating a disease or condition in which regeneration of epithelial, mesenchymal and/or endothelial tissue is beneficial in a subject in need thereof, the method comprising administering to the subject a therapeutically effective amount of the pharmaceutical composition of some embodiments of the present invention, thereby treating the disease or condition in which regeneration of epithelial, mesenchymal and/or endothelial tissue is beneficial.

According to an aspect of some embodiments of the present invention there is provided a method of treating a pulmonary disorder or injury in a subject in need thereof, the method comprising administering to the subject a therapeutically effective amount of the pharmaceutical composition of some embodiments of the present invention, thereby treating the pulmonary disorder or injury.

According to an aspect of some embodiments of the present invention there is provided a pharmaceutical composition of some embodiments of the present invention for use in treating a disease or condition in which regeneration of epithelial, mesenchymal and/or endothelial tissue is beneficial in a subject in need thereof.

According to an aspect of some embodiments of the present invention there is provided a pharmaceutical composition of some embodiments of the present invention for use in treating a pulmonary disorder or injury in a subject in need thereof.

According to an aspect of some embodiments of the present invention there is provided a cell bank comprising a plurality of cell populations isolated from mammalian fetal pulmonary tissues, wherein the fetal pulmonary tissues are at a developmental stage essentially corresponding to that of a human pulmonary organ/tissue at a gestational stage selected from a range of about 20 to about 22 weeks of gestation, and wherein the plurality of cell populations have been HLA typed to form an allogeneic cell bank, each individually disposed within separate containers.

According to some embodiments of the invention, the gestational stage is 20 to 21 weeks of gestation.

According to some embodiments of the invention, the gestational stage is 21 to 22 weeks of gestation.

According to some embodiments of the invention, the mammalian fetal pulmonary tissue is a human tissue.

According to some embodiments of the invention, the isolated population of cell suspension comprises a heterogeneous population of cells.

According to some embodiments of the invention, the isolated population of cell suspension comprises progenitor cells.

According to some embodiments of the invention, the progenitor cells are selected from the group consisting of epithelial progenitor cells, mesenchymal progenitor cells and endothelial progenitor cells.

According to some embodiments of the invention, the cells comprise a cytokeratin 5+ (CK5+) marker expression.

According to some embodiments of the invention, the cells comprise a cytokeratin 5+ (CK5+) and cytokeratin 14+ (CK14+) marker expression.

According to some embodiments of the invention, the cells comprise a c-Kit+ CD45− CD34− CD31− CD326− CD271− marker expression.

According to some embodiments of the invention, the cells comprise a c-Kit+ CD34+ CD31+ marker expression.

According to some embodiments of the invention, the cells comprise a c-Kit+ CD34+ CD326+ marker expression.

According to some embodiments of the invention, the cells comprise a CD34+ CD31+ CD14+ CD45+ marker expression.

According to some embodiments of the invention, the cells comprise a CD34+ CD31+ CD45− CD105+ marker expression.

According to some embodiments of the invention, the cells comprise a nestin+ and/or a calcitonin gene related protein+ (CGRP+) marker expression.

According to some embodiments of the invention, the cells comprise an alpha smooth muscle actin+ (alpha-SMA+) and/or a Vimentin+ marker expression.

According to some embodiments of the invention, the cells are capable of regenerating a structural/functional pulmonary tissue.

According to some embodiments of the invention, the structural/functional pulmonary tissue comprises generation of a chimeric lung.

According to some embodiments of the invention, the chimeric lung comprises formation of alveolar, bronchial and/or bronchiolar structures, and/or vascular structures.

According to some embodiments of the invention, the structural/functional pulmonary tissue comprises an ability to synthesize surfactant and/or an ability to transportions.

According to some embodiments of the invention, the cells are capable of regenerating an epithelial, mesenchymal and/or endothelial tissue.

According to some embodiments of the invention, the cells are CFTR expressing epithelial cells.

According to some embodiments of the invention, the epithelial tissue is selected from the group consisting of a lung tissue, a gastrointestinal tract tissue, a reproductive organ tissue, a urinary tract tissue, a renal tissue, a skin tissue, a cardiac tissue, an ischemic tissue and a brain tissue.

According to some embodiments of the invention, the mesenchymal tissue is selected from the group consisting of a lymphatic tissue, a circulatory system tissue and a connective tissue.

According to some embodiments of the invention, the endothelial tissue is selected from the group consisting of a lymphatic tissue and a circulatory system tissue.

According to some embodiments of the invention, the method further comprises conditioning the subject under sublethal, lethal or supralethal conditioning protocol prior to the administering.

According to some embodiments of the invention, the administering is effected by an intravenous route.

According to some embodiments of the invention, the administering is effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the method further comprises treating the subject with an immunosuppressive regimen prior to, concomitantly with or following the transplantation.

According to some embodiments of the invention, the composition is formulated for intravenous administration.

According to some embodiments of the invention, the composition is formulated for administration via a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to some embodiments of the invention, the pharmaceutical composition further comprises a sublethal, lethal or supralethal conditioning protocol.

According to some embodiments of the invention, the sublethal, lethal or supralethal conditioning is selected from the group consisting of a total body irradiation (TBI), a partial body irradiation, a myeloablative conditioning, a co-stimulatory blockade, a chemotherapeutic agent and/or an antibody immunotherapy.

According to some embodiments of the invention, the conditioning comprises naphthalene treatment.

According to some embodiments of the invention, the conditioning further comprises total body irradiation (TBI).

According to some embodiments of the invention, the conditioning comprises total body irradiation (TBI).

According to some embodiments of the invention, the TBI comprises a single or fractionated irradiation dose within the range of 1-7.5 Gy.

According to some embodiments of the invention, the subject is a human subject.

According to some embodiments of the invention, the mammalian fetal pulmonary tissue is a human tissue.

According to some embodiments of the invention, the isolated population of cell suspension is non-syngeneic with the subject.

According to some embodiments of the invention, the isolated population of cell suspension is allogeneic with the subject.

According to some embodiments of the invention, the allogeneic cells are selected from the group consisting of HLA identical, partially HLA identical and HLA non-identical with the subject.

According to some embodiments of the invention, the isolated population of cell suspension is xenogeneic with the subject.

According to some embodiments of the invention, the pulmonary disorder or injury is selected from the group consisting of cystic fibrosis, emphysema, asbestosis, chronic obstructive pulmonary disease (COPD), pulmonary fibrosis, idiopatic pulmonary fibrosis, pulmonary hypertension, lung cancer, sarcoidosis, acute lung injury (adult respiratory distress syndrome), respiratory distress syndrome of prematurity, chronic lung disease of prematurity (bronchopulmonarydysplasia), surfactant protein B deficiency, congenital diaphragmatic hernia, pulmonary alveolar proteinosis, pulmonary hypoplasia and lung injury.

According to some embodiments of the invention, the disease or condition in which regeneration of epithelial, mesenchymal and/or endothelial tissue is beneficial is selected from the group consisting of pulmonary disorder, disease or injury; renal disorder, disease or injury; hepatic disorder, disease or injury; cardiac disorder, disease or injury; gastrointestinal tract disorder, disease or injury; skin disorder, disease or injury; and brain disorder, disease or injury.

According to some embodiments of the invention, the disease or condition in which regeneration of epithelial tissue is beneficial is selected from the group consisting of chronic ulcers, inflammatory bowel disease (IBD), Crohn's disease, ulcerative colitis, Alzheimer's disease, wound healing defects, cancer, chronic obstructive pulmonary disease (COPD), pulmonary fibrosis, idiopatic pulmonary fibrosis, pulmonary hypertension, lung cancer, sarcoidosis, acute lung injury (adult respiratory distress syndrome), respiratory distress syndrome of prematurity, chronic lung disease of prematurity (bronchopulmonarydysplasia), surfactant protein B deficiency, congenital diaphragmatic hernia, pulmonary alveolar proteinosis, pulmonary hypoplasia, lung injury and corneal degeneration.

According to some embodiments of the invention, the disease or condition in which regeneration of mesenchymal tissue is beneficial is selected from the group consisting of heart disease or condition, diabetes, deafness, Crohn's disease, autoimmune disorders, leukemia, cancer, sickle cell disease, amyotrophic lateral sclerosis and metabolic disorders.

According to some embodiments of the invention, the disease or condition in which regeneration of endothelial tissue is beneficial is selected from the group consisting of vascular disease, ischemia, sickle cell disease, cardiovascular disease, atherosclerosis, diabetes and autoimmune disorders, According to some embodiments of the invention, the cell bank further comprises a catalogue which comprises information about the HLA typed cells of the plurality of cell populations.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-R depict growth and development of human embryonic precursor tissues harvested at different gestational time points. Human embryonic tissues were implanted under the renal capsule of NOD-SCID mice. The implants were evaluated macroscopically or by immunohistological staining after 8 weeks. FIG. 1A is a summary of macroscopic size of implants from different gestational time points implants: Mean (±SD) size, based on long (L) and short (W) axes and height (H) of the implants, 6-8 weeks post-transplant (data shown are average of six independent experiments); FIG. 1B is a photograph illustrating a typical macroscopic appearance of the implants harvested at 20 w of gestation; FIGS. 1C-F are photographs of microscopic hematoxylin and eosin stain (H&E) examination of the implant derived from 20 w tissue, showing normal appearance of alveolar ducts, alveoli, trachea covered with ciliated epithelium, muscular layer and cartilage, and alveolar/epithelial monolayer; FIGS. 1G-H are photographs illustrating immunostaining for surfactant protein C (sp-C) in red, and cytokeratin-18 (CK-18) in green, at lower (FIG. 1G) and higher magnification (FIG. 1H); FIG. 1I is a photograph illustrating immunostaining for CFTR-cystic fibrosis transmembrane regulator in red and CK-18 in green; FIGS. 1J-R are photographs illustrating typical H&E staining of implants derived from 15 w (FIGS. 1J-L), 18 w (FIGS. 1P-R), and 24 w (FIGS. 1M-O) tissues, respectively. Arrows indicate cyst. In (FIG. 1M) macroscopic image of a cyst is illustrated.

FIGS. 2A-O depict identification of early progenitors and their niches in the human embryonic lung. FIGS. 2A-D are photographs illustrating H&E staining of human embryonic lung tissues at different gestational time points, revealing bronchial and bronchiolar structures without any alveolar structures; FIGS. 2E-F are photographs illustrating immunohistological staining showing high expression of CK5+ cells in large airways and co-expression of CK5 and CK14 in the large bronchus. Arrows and arrow heads indicate regions with high and low CK5 expression, respectively. CK5+ cells in bronchial and developing alveolar structures are associated with rich innervation, illustrated by contact with nestin+ and CGRP+ cells (FIG. 2G), as well as by staining for neurofilaments (NF) (FIG. 2H); FIG. 2I is a photograph illustrating alpha-smooth muscle actin positive cells; FIG. 2J is a photograph illustrating Vimentin$^+$ mesenchymal cells residing in close proximity to the CK5$^+$ progenitors; FIGS. 2K-N are photograph illustrating staining for CK5 (red) at different time points including 15 (FIG. 2K), 17 (FIG. 2L), 20 (FIG. 2M), and 22 (FIG. 2N) weeks of human gestation demonstrating differences in CK5 expression level; FIG. 2O is a graph illustrating quantitative morphometric analysis of tissue area occupied by CK5+ progenitors showing significantly (t-test) higher levels at 20-22 weeks one diamond represents a p-value that is non-significant, two diamonds represent p<0.002).

FIGS. 2P-Z depict FACS analysis of early non-hematopoietic progenitors in human embryonic lung tissue harvested at different gestational time points. FIGS. 2P-Q illustrate representative FACS analysis of 20 w lung cells showing double staining with anti-CD45 and anti-CD34. Three subpopulations within the non-hematopoietic CD45− cells, including CD45−CD34$^{high}$, CD45− CD34$^{intermediate}$, and CD45− CD34$^{neg}$ cells, are depicted; FIGS. 2R-T illustrate double staining with anti-CD117 (c-kit) and anti-CD271 (mesenchymal differentiation marker) revealing the level of each subpopulation; FIGS. 2U-Z illustrate the percentage of single positive CD117+ cells within the CD45− CD34$^{neg}$ population in different human embryonic lung tissues.

FIGS. 4A-K depict triple staining with E-cadherin, CD34 and CD117 prior to transplantation of lung tissues harvested at 21 weeks. FIG. 4A illustrates single staining for CD34; FIG. 4B illustrates single staining for CD117; FIG. 4C illustrates a merge with E-cadherin staining. Panoramic images of two neighboring regions, which include large bronchus and developing alveolar structures are depicted. The majority of CD34$^+$ cells in the region of developing alveolar structures co-express CD117 (FIGS. 4D-G), while in the large airway region, rare single positive CD117$^+$ cells may be seen in close proximity to blood vessels (FIGS. 4H-K).

FIGS. 5A-D are photographs depicting a panoramic view of three neighboring fields in 20 w human lung illustrating presence of CK5 positive regions (red, FIG. 5A) with different intensity of expression, which are surrounded by blood vessels (blue, FIG. 5B) and alpha-SMA positive cells (green, FIG. 5C) both in large bronchus and in developing alveoli, (blue, FIG. 5B), suggestive of distinct niches (the overlay of all 3 compartments is shown in FIG. 5D). Bar=50 µm.

FIGS. 6A-L depict polychromatic FACS analysis of two different adult human lung samples. Polychromatic FACS analysis of adult human lung tissues was performed in parallel to human embryonic lung tissues. Single cell suspension was stained, after enzymatic dissociation with collagenase and dispase of the tissues, and stained by CD34 (specific for hematopoietic and endothelial progenitors), CD45 (hematopoietic cells), CD31 (marker for endothelial cells), CD117 (c-KIT, to identify early progenitors), CD271 (NGFR—mesenchymal stem cell marker), and CD326 (EP-CAM− epithelial differentiation marker) specific antibodies or equivalent isotype controls. In both samples, CD34$^+$ and CD34$^-$ populations were identified (FIGS. 6A, 6D, 6G and 6J). Prominent differences were observed between adult and embryonic lung tissues. Much lower levels of CD34$^+$ cells were identified in adult lungs. When tested for the presence of the c-kit$^+$ population, very small CD34$^+$CD117$^+$ and CD34$^-$CD117$^+$ populations were identified (FIGS. 6B, 6E, 6H and 6K); the majority of CD34$^+$CD117$^+$ cells were positive for the CD31 marker and only small percentage negative for CD31 marker (FIGS. 6C, 6F, 6I and 6L), and most of CD34$^-$CD117$^+$ population was found negative for CD31 and CD326 (FIGS. 6F and 6L).

FIGS. 7A-I depict FACS analysis of 20 w HEL, demonstrating CD45−CD34+and CD45−CD34− subpopulations (FIG. 7A). CD117$^+$ staining within the CD34 positive (FIG. 7B) and negative (FIG. 7C) cell subpopulations. The majority of CD34+CD117+ subpopulation is positive for CD31 or CD326 markers (FIGS. 7D, 7F-G). The majority of CD34$^-$ CD117$^+$ cells are negative for CD31 and CD326 markers (FIGS. 7E, 7H-I). In FIGS. 7F-I, representative histograms are demonstrated, where red line marks isotype control of CD31 and CD326 markers, blue line shows the CD34+ CD31+ subpopulation and green line shows the CD34+ CD326+ subpopulation (FIGS. 7F-G); in FIGS. 7H-I, blue line marks the CD34−CD31+ subpopulation and green line marks the CD34−CD326+ subpopulation. These findings confirm the existence of two different CD117$^+$ populations, as demonstrated by immunohistochemistry.

FIGS. 9A-D depict analysis of 20 w human lung for the presence of early and late endothelial progenitors (EPC). This figure identifies presence of two minor distinct CD34+ CD31+ subpopuations (FIG. 9B). The first one identified by positive staining for CD14 and CD45 (FIG. 9C), whereas the second subpopulation is CD45−CD105+ (FIG. 9D).

FIGS. 10A-C are photographs illustrating a typical H&E staining demonstrating the poor growth of E14 (FIG. 10A) and E17 (FIG. 10B) lung tissues at 12 weeks post transplant under the renal capsule of SCID mice (n=7), compared to marked growth and differentiation attained following E16 mouse embryonic implants (n=5) (FIGS. 10C-E); FIGS. 10D-E are photographs illustrating H&E staining demonstrating large airways (large arrows) and alveolar structures (small arrows) and cytokeratin staining in implants of E16 mouse fetal lung.

FIGS. 11A-Y depict characterization of lung progenitors in E16 mouse embryonic lung prior to transplantation. FIG. 11A is a photograph illustrating H&E staining of E16 embryonic lung demonstrating immature structures and absence of alveolar structures; FIG. 11B is a photograph illustrating CK-5 positive cells (blue) in E16 mouse tissue, similar to human embryonic lung, have higher expression in large airways. Numerous neuroepithelial bodies, stained positively by CGRP (red), and tyrosine hydroxylase (TH, green) are found within the entire sample, and are localized in niches; FIG. 11C is a photograph illustrating CCSP-positive cells are found in the regions of large airways, also rich in nestin-positive cells and surrounded by alpha-SMA positive cells (FIG. 11D, white arrows), suggestive of stem cell niches; FIGS. 11E-G are representative polychromatic FACS analysis of CD45$^-$CD31$^-$CD326$^+$ CD24$^+$CD49f$^+$ CD104$^+$ cells in E13, E14, E15 and E16 lung-derived single cell suspensions following treatment with collagenase and dispase (n=10, 10, 12 and 10 respectively, values represent mean±SD from two different experiments). A significantly higher abundance of this cell population in E15-16 lung is demonstrated (p<0.007); FIG. 11Y is a summary of CD45$^-$ CD31$^-$ CD326$^+$ CD24$^+$CD49f$^+$CD104$^+$ cell levels showing statistical significance calculated by Student's t-test (one diamond represents p<0.037, two diamonds represent p<0.007, cell gating strategies are described in the Examples section hereinbelow).

FIGS. 12A-F are photographs depicting immunohistochemical staining of adult C57Bl lung, demonstrating presence of nestin and CGRP (FIGS. 12A-B), similar to their expression in stem cell niches in the embryonic mouse lung (FIG. 12A—lower magnification—bar=50 μm, FIG. 12B—higher magnification—bar=20 μm). Box in (FIG. 12A) indicates the position of the enlargement shown in (FIG. 12B); FIGS. 12C-F are photographs illustrating triple staining of adult C57Bl lung for alpha-SMA (green, FIG. 12C), CGRP (red, FIG. 12D) and E-cadherin (blue overlay with alpha-SMA and CGRP, FIG. 12E), bar=50 μm; and FIG. 12F illustrates an enlarged area of the square marked in FIG. 12E, bar=20 μm.

FIGS. 13A-D depict fluorescent microscopy of chimeric lungs under low power magnification demonstrating different numbers of foci of engrafted GFP+ cells following different conditioning regimens. FIGS. 13A-C are photographs of representative images of chimeric lungs of animals treated with 6 Gy TBI (FIG. 13A), NA only (FIG. 13B), and NA plus 6 GY TBI (FIG. 13C); FIG. 13D are quantitative morphometric analysis of GFP+ patches of engrafted cells per $mm^3$, following different conditioning regimens (n=10 in each group). The results of 3 independent experiments are presented.

FIGS. 14A-L are photographs depicting staining of CCSP+ cells before and after infusion of E16 cells. FIG. 14A illustrates lumens of large airways of untreated control mice; FIG. 14B illustrates lungs of experimental animals 1 day after conditioning with naphthalene and 6 Gy TBI, showing peeling of CCSP+ cells; FIG. 14C illustrates lungs of animals conditioned with naphthalene and 6 Gy TBI 30 days after infusion of E16 cells, showing marked regeneration of the epithelial layer with engrafted GFP+ cells (green) in the bronchial lumens, which are vascularized, as indicated by staining for V-E cadherin; FIGS. 14D-L illustrate that transplanted cells (FIGS. 14D-F) incorporate into the epithelial layer, regenerate CCSP+ cells (red), are able to produce surfactant (FIGS. 14G-I), and exhibit ion transport potential, as indicated by staining for CFTR (FIGS. 14J-L).

FIGS. 15A-C are photographs depicting 2-photon microscopy revealing chimerism level in implanted lungs. Representative 2-photon microscopy lung images of transplanted mice at 6 (FIGS. 15A-B) and 16 (FIG. 15C) weeks after transplantation, without (FIG. 15A), and with co-staining of blood vessels with non-targeted Quantum dots (red) (FIG. 15B).

FIGS. 16A-L are photographs depicting immunohistological characterization of chimeric lungs at 16 weeks after transplantation. FIGS. 16A-D are representative images of chimeric lung stained with anti-GFP antibody (green), anti-CD31 antibody (red), and anti-pancytokeratin antibody (blue), demonstrating incorporation of GFP+ cells in vascular and epithelial compartments of transplanted lungs, without signs of scarring or fibrosis; FIGS. 16E-H are representative images of chimeric lungs stained with anti-GFP (green) and anti AQP-5 antibody (red), showing incorporation of transplanted tissue into the gas-exchange surface of type I alveocytes; FIGS. 16I-L are images of chimeric lung stained with anti-GFP (green), anti-CD31 (red) and anti-sp-C antibody (blue), demonstrating type II alveocyte participation of transplanted cells in surfactant synthesis.

FIGS. 17A-E are photographs depicting appearance of control non-transplanted C57Bl lung analyzed by 2-photon microscopy, bar=90 μm (control lung, FIG. 17A) and triple staining of chimeric lung with anti-GFP (green), anti-cytokeratin (blue), and anti-CD31 antibodies, demonstrating chimerism in both epithelial and vascular compartments of the lung, and full incorporation in the structures, without signs of scarring or fibrosis, under low magnification, bar=200 μm (FIGS. 17B-E). In green fluorescent channel GFP+ chimeric foci are indicated by dotted line (FIG. 17B). In red and blue channels the same chimeric regions are also indicated by dotted line, demonstrating smooth transition from recipient to donor tissue in both vascular (FIG. 17C) and epithelial (FIG. 17D) compartments, and overlay of all the layers is shown in (FIG. 17E).

FIGS. 18A-I are photographs depicting engraftment and incorporation of human derived lung cells into the mouse lung at different time points post transplantation. FIGS. 18A-C illustrate chimerism in the mouse lung at 6 weeks post transplantation, showing staining for mouse MHC (red) and human tissue positive for MNF-116 (green) under low magnification; FIGS. 18D-F illustrate chimerism in the mouse lung at 6 weeks post transplantation, showing staining for mouse MHC (red) and human tissue positive for MNF-116 (green), under high magnification; FIGS. 18G-I illustrate an additional field, stained as in (FIGS. 18D-F).

FIGS. 19A-F are photographs depicting typical chimerism in the lung bronchus of transplanted mouse at 7 weeks post transplant. FIGS. 19A and 19D illustrate human cells originating from human embryonic cells which were selectively stained with a cocktail of mouse anti-human antibodies including anti-MNF (epithelial marker), anti-human Vimentin 9 (typical of stromal cells), and mouse anti-human CD31 (endothelial cell marker) labeled with Daylight 488 (green); FIGS. 19B and 19E illustrate cells of mouse origin in the mouse lung which were stained with Banderia lectin labeled with Alexa-fluor 546 (red). The latter is known to bind to a-Gal expressed on mouse epithelial and endothelial cells. Upper panel shows chimeric field under low magnification (FIG. 19C), the lower panel shows the same region under high magnification (FIG. 19F).

FIGS. 20A-F are photographs depicting typical chimerism in the lung alveoli of a transplanted mouse at 7 weeks post transplant. FIGS. 20A and 20D illustrate human cells originating from human embryonic cells which were selectively stained with a cocktail of mouse anti-human antibodies including anti-MNF (epithelial marker), anti-human Vimentin 9 (typical of stromal cells), and mouse anti-human CD31 (endothelial cell marker) labeled with Day light 488 (green); FIGS. 20B and 20E illustrate cells of mouse origin in the mouse lung which were stained with Banderia lectin labeled with Alexa-fluor 546 (red). The latter is known to bind to a-Gal expressed on mouse epithelial and endothelial cells, but not on their human counterparts. Upper panel shows chimeric field under low magnification (FIG. 20C); the lower panel shows the same region under high magnification (FIG. 20F).

FIGS. 21A-C are photographs depicting incorporation of human cells into the lung parenchyma. FIG. 21A illustrates human cells which were stained (green) with a mixture of anti-human antibodies including anti-MNF117, anti-V9, anti-CD31 as described above, and with rabbit anti-cytokeratin antibody (red), which stains both mouse and human cytokeratin (FIG. 21B). Merging of both colors demonstrates human cells within the lung parenchyma (FIG. 21C).

FIGS. 22A-C are photographs depicting incorporation of human cells into the lung gas-exchange surface. Human cells were stained (green) with a mixture of anti-human antibodies including anti-MNF117, anti-V9, and anti-CD31, as described above (FIG. 22A) and with goat anti-AQP-5 (red), which stains both mouse and human AQP-5 (FIG. 22B). Merging of both colors demonstrates human cells within the lung gas-exchange surface (FIG. 22C).

FIGS. 23A-F are photographs depicting that engrafted human lung cells within the alveoli of a chimeric mouse participate in production of surfactant. Human cells were stained (green) with a mixture of anti-human antibodies including anti-MNF117, anti-V9, and anti-CD31 as described above (FIGS. 23A and 23D), and with rabbit anti-SPC antibody (red), which stains both mouse and human surfactant protein C (FIG. 23B). Merging of both colors demonstrates participation of the transplanted human tissue in production of surfactant (FIG. 23C). The lower panel (FIGS. 23D-F) shows staining at high magnification of the square area denoted in (FIG. 23C).

FIGS. 24A-H are photographs depicting engraftment of 20 w human lung derived single cell suspension stained with CMTMR in the lung of a NOD-SCID mouse, bar=500 µm (FIG. 24A); GFP+ patches denoting lung cells originating from transplanted mouse embryonic lung cells in the syngeneic transplantation model, bar=1 mm (FIG. 24B); FIGS. 24C-E illustrate control staining with mouse anti-human cytokeratin MNF 116 antibody (green, FIG. 24C) and rat anti-mouse MHC (red, FIG. 24D) of human embryonic lung tissue, which is positive to MNF116 and negative to mouse MHC (overlay of two is shown in FIG. 24E); FIGS. 24F-H illustrate control staining of mouse lung cells with anti-human MNF116 anti-mouse MHC antibodies, demonstrating negative staining for MNF116 and positive staining for mouse MHC, bar=50 µm.

FIGS. 25A-D are photographs depicting long term follow-up of mice implanted with E16 mouse embryonic lung tissue showing no evidence of teratoma. FIG. 25A illustrates a macroscopic appearance of the transplanted lung one year after transplantation showing smooth borders and absence of tumors; FIGS. 25B-C illustrate H&E staining showing normal morphology of the transplanted lung under lower (FIG. 25B) and higher magnification (FIG. 25C) one year after transplantation; FIG. 25D illustrates coronal views of in-vivo lung CT images of a typical transplanted animal showing normal radiologic appearance of the experimental lung.

DESCRIPTION OF SPECIFIC EMBODIMENTS OF THE INVENTION

Figures 3A, 3B, 3C:
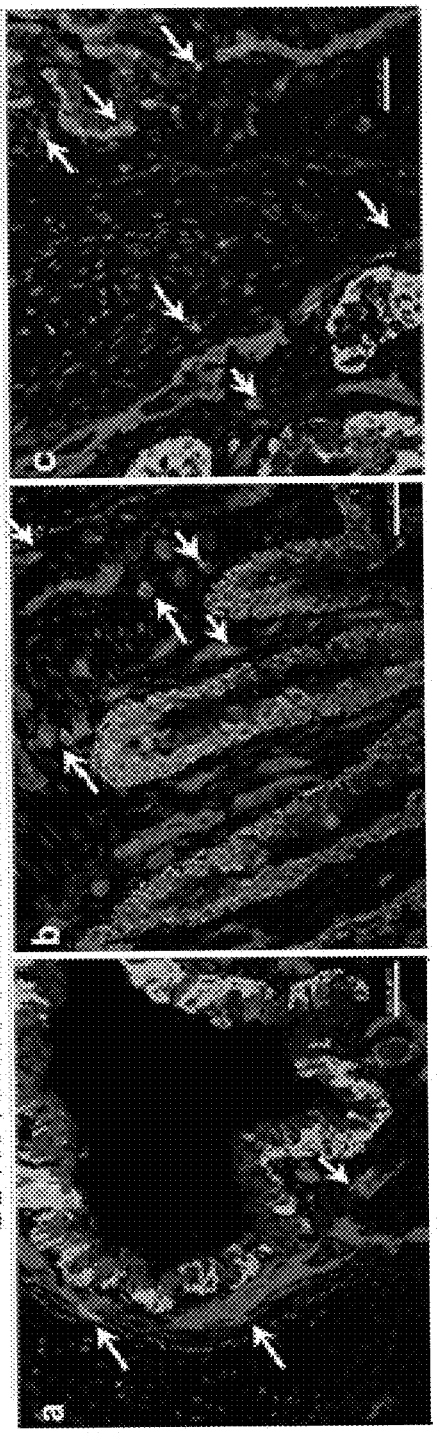
FIGS. 3A-C depict triple staining with CK5, ULEX lectin, and CD117 prior to transplantation of lung tissues harvested at 21 weeks. Central airway (FIG. 3A) and main bronchus (FIG. 3B) showing high expression of CK5 in large airways, surrounded by large blood vessels. Rare CD117$^+$ cells reside in perivascular spaces. In the region of smaller airways (FIG. 3C), lower expression of CK5 is observed, in close contact with smaller blood vessels, while numerous CD117$^+$ cells reside within these blood vessels (pink; double positive for the ULEX lectin and CD117).
Figures 8A, 8B, 8C, 8D:
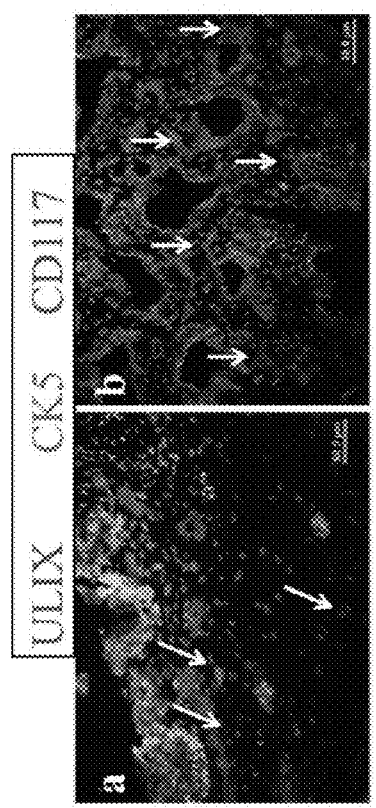
FIGS. 8A-D depict immunohistological staining of 15 w (FIGS. 8A-B) and 17 w (FIGS. 8C-D) HEL for ulix-vascular marker (blue), CK5 (green) and CD117 (red), showing the dual CD117 expression pattern. Several single CD117$^+$ cells are found in close proximity to large airways and blood vessels, while most of them are co-localized within blood vessels around the developing alveolar structures.

The present invention, in some embodiments thereof, relates to mammalian embryonic pulmonary cells and, more particularly, but not exclusively, to the use of same for therapeutic applications.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Previous studies have defined "windows" for transplantation of human and pig embryonic tissues of different organs, including kidney, liver, pancreas, lung and heart. Thus, for example, the lung 'window' was shown to occur at 42 to 80 days of porcine gestational age [PCT Publication No. WO 2006/038211; Eventov-Friedman S. et al., Proc Nat Acad of Sciences. (2005) 102(8): 2928]. Additional studies suggest that early progenitors derived from adult tissues, such as the bone marrow or from the umbilical cord blood, amniotic fluid or placenta, including mesenchymal stem cells, endothelial progenitors or circulating fibrocytes and a variety of other populations, could structurally engraft and differentiate as airways and alveolar epithelial cells or as vascular endothelial or interstitial lung cells and could be utilized in repair and regeneration of injured or diseased lungs.

While reducing the present invention to practice, the present inventors have identified a unique cell population of embryonic lung tissue, obtained from a 'window' of 20-22 weeks of human gestational age, which comprises a multitude of lung progenitor cells which can be used for repair of injured/diseases lungs. Surprisingly a suspension of such a cell population, which doesn't maintain a tissue structure, can be used to regenerate epithelial, mesenchymal and endothelial lung tissues.

As is shown hereinbelow and in the Examples section which follows, the present inventors have illustrated, for the first time, that an isolated cell population suspension, namely at 20-22 weeks of human gestation (see Example 1, in the Examples section which follows) can be used to regenerate lung tissue and resume lung functionality upon administration.

Thus, the present inventors have shown that an isolated cell population of 20-22 weeks of human gestation and a similar canalicular 'window' of mouse embryonic lung tissue, defined at 15-16 days of gestation (see Example 1, in the Examples section which follows), exhibited the highest levels of putative lung precursors (including epithelial, endothelial, and mesenchymal progenitor cells) compared to tissues harvested at earlier or later gestational time points (see Example 1, in the Examples section which follows). Furthermore, administration (e.g. intravenous administration) of single cell suspensions obtained from tissues of this gestational window achieved a remarkable lung repair. Specifically, the lung precursor cells homed, differentiated and integrated in injured lungs of mice resulting in formation of an entire respiratory unit including formation of new epithelial cells and new vasculature (see Example 2, in the Examples section which follows). Furthermore, this process was markedly enhanced upon further conditioning of the recipient mice using naphthalene treatment, with or without sub-lethal total body irradiation (TBI), leading to substantial and durable chimerism in different cell lineages of the injured lungs (see Example 2, in the Examples section which follows). Taken together, these results substantiate the use of single cell suspensions of human embryonic lung precursor tissue, harvested at 20-22 weeks gestation, for the treatment of epithelial, mesenchymal and endothelial conditions including lung disease and injury.

Thus, according to one aspect of the present invention, there is provided a pharmaceutical composition comprising as an active ingredient an isolated population of cell suspension from a mammalian fetal pulmonary tissue, wherein the fetal pulmonary tissue is at a developmental stage corresponding to that of a human pulmonary organ/tissue at a gestational stage selected from a range of about 20 to about 22 weeks of gestation.

The phrase "isolated population of cell suspension" as used herein refers to cells which have been isolated from their natural environment (e.g., the human body) are extracted from the tissue while maintaining viability but do not maintain a tissue structure (i.e., no vascularized tissue structure) and are not attached to a solid support.

Depending on the application, the method may be effected using an isolated population of cell suspension which comprises syngeneic or non-syngeneic cells (with respect to a subject).

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to a cell which is derived from pulmonary tissue of a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other.

The present invention envisages that xenogeneic cells are derived from a variety of species, as described in further detail hereinbelow.

Cells or tissues of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to an embodiment of the present invention, the subject is a human being and the isolated population of cells is from a human origin (e.g. human fetus).

Depending on the application and available sources, the cells of the present invention may be naïve or genetically modified. Such determinations are well within the ability of one of ordinary skill in the art.

Since non-sygneneic cells are likely to induce an immune reaction when administered to the subject several approaches have been developed to reduce the likelihood of rejection of non-syngeneic cells. These include either suppressing the recipient immune system or encapsulating the non-autologous cells in immunoisolating, semipermeable membranes before transplantation. Alternatively, cells may be uses which do not express xenogenic surface antigens, such as those developed in transgenic animals (e.g. pigs).

The phrase "pulmonary tissue" as used herein refers to a lung tissue or organ. The pulmonary tissue of the present invention may be a full or partial organ or tissue. Thus, the pulmonary tissue of the present invention may comprise the right lung, the left lung, or both. The pulmonary tissue of the present invention may comprise one, two, three, four or five lobes (from either the right or the left lung). Moreover, the pulmonary tissue of the present invention may comprise one or more lung segments or lung lobules. Furthermore, the pulmonary tissue of the present invention may comprise any number of bronchi and bronchioles (e.g. bronchial tree) and any number of alveoli or alveolar sacs.

According to one embodiment of the present invention, the pulmonary tissue is at a developmental stage corresponding to that of a human pulmonary organ/tissue at a gestational stage of about 20 to about 21 weeks of gestation, about 20.5 to about 21.5 weeks of gestation, about 20 to about 22 weeks of gestation, about 20.5 to about 22.5 weeks of gestation, about 21 to about 22 weeks of gestation, about 21.5 to about 22.5 weeks of gestation.

According to a specific embodiment, the pulmonary tissue is at a developmental stage corresponding to that of a human pulmonary organ/tissue at a gestational stage of about 20 to about 22 weeks of gestation.

According to another specific embodiment, the pulmonary tissue is at a developmental stage corresponding to that of a human pulmonary organ/tissue at a gestational stage of about 21 to about 22 weeks of gestation.

According to another specific embodiment, the pulmonary tissue is at a developmental stage corresponding to that of a human pulmonary organ/tissue at a gestational stage of about 20 to about 21 weeks of gestation.

As mentioned, the pulmonary tissue of the present invention is obtained from a mammalian organism.

Thus, the pulmonary tissue of the present invention may be derived from any mammal. Suitable species origins for the pulmonary tissue comprise the major domesticated or livestock animals, and primates, which have been extensively characterized with respect to correlation of stage of differentiation with gestational stage. Such animals include porcines (e.g. pig), bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

According to a specific embodiment, the pulmonary tissue is derived from a human being.

According to a specific embodiment, the pulmonary tissue is derived from a non-human organism.

Various methods may be employed to obtain a pulmonary tissue at a developmental stage essentially corresponding to that of a human derived pulmonary tissue, as presently taught. Obtaining such a pulmonary tissue may be effected by harvesting the pulmonary tissue from a developing fetus at such a stage of gestation (i.e. corresponding to human 20-22 weeks of gestation), e.g. by a surgical procedure. It will be understood by those of skill in the art that the gestational stage of an organism is the time period elapsed following fertilization of the oocyte generating the organism.

Alternatively, a pulmonary tissue at a desired developmental stage may be obtained by in-vitro culture of cells, organs/tissues. Such controlled in-vitro differentiation of cells, tissues or organs is routinely performed, for example, using culturing of embryonic stem cell lines to generate cultures containing cells/tissues/organs of desired lineages. For example, for generation of pulmonary lineages, refer for example, to Otto W R., 1997. Int J Exp Pathol. 78:291-310.

The following table provides an example of the gestational stages of human and porcine pulmonary tissues at which these can provide pulmonary tissues which are essentially at corresponding developmental stages:

TABLE 1

Corresponding gestational stages of pigs and humans

| Gestational stage of porcine pulmonary tissue (days) | Gestational stage of human pulmonary tissue (days*) |
|---|---|
| 18 | 44 |
| 20 | 49 |
| 22 | 54 |

TABLE 1-continued

Corresponding gestational stages of pigs and humans

| Gestational stage of porcine pulmonary tissue (days) | Gestational stage of human pulmonary tissue (days*) |
|---|---|
| 23 | 56-57 |
| 25 | 61-62 |
| 26 | 63 |
| 28 | 68-69 |
| 31 | 75 |
| 38 | 92 |
| 42 | 102 |
| 46 | 112 |
| 49 | 119 |
| 56 | 136 |
| 62 | 151 |
| 72 | 175 |
| 80 | 195 |
| 88 | 214 |

The gestational stage (in days) of a pulmonary tissue belonging to a given species which is at a developmental stage essentially corresponding to that of a porcine pulmonary tissue can be calculated according to the following formula: [gestational stage of porcine pulmonary tissue in days]/[gestational period of pig in days] × [gestational stage of pulmonary tissue of given species in days]. Similarly, the gestational stage (in days) of a pulmonary tissue belonging to a given species which is at a developmental stage essentially corresponding to that of a human pulmonary tissue can be calculated according to the following formula: [gestational stage of human pulmonary tissue in days]/[gestational period of humans in days] × [gestational stage of pulmonary tissue of given species in days]. The gestational stage of pigs is about 115 days and that of humans is about 280 days.
*for week calculation divide the numbers by 7.

After the fetal pulmonary tissue is obtained, the present invention further contemplates generation of an isolated population of cells therefrom.

As used herein, "single cell suspension" refers to a fetal pulmonary single cell suspension comprising single cells or cell aggregates of no more than 5, 10, 50, 100, 200, 300, 400, 500, 1000, 1500, 2000 cells in an aggregate.

The single cell suspension of the present invention may be obtained by any mechanical or chemical (e.g. enzymatic) means. Several methods exist for dissociating cell clusters to form single cell suspensions from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Acutase and the like) or a combination of both.

Thus, for example, enzymatic digestion of fetal pulmonary tissue into isolate cells can be performed by subjecting the tissue to an enzyme such as type IV Collagenase (Worthington biochemical corporation, Lakewood, N.J., USA) and/or Dispase (Invitrogen Corporation products, Grand Island N.Y., USA). For example, the pulmonary tissue may be enzyme digested by finely mincing tissue with a razor blade in the presence of e.g. collagenase, dispase and $CaCl_2$ at 37° C. for about 1 hour. The method may further comprise removal of nonspecific debris from the resultant cell suspension by, for example, sequential filtration through filters (e.g. 70- and 40-1 μm filters), essentially as described under "General Materials and Experimental Methods" of the Examples section which follows.

Furthermore, mechanical dissociation of fetal pulmonary tissue into isolate cells can be performed using a device designed to break the tissue to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the tissue/cells under an inverted microscope.

Following enzymatic or mechanical dissociation of the fetal pulmonary tissue, the dissociated fetal pulmonary cells are further broken to small clumps using 200 μl Gilson pipette tips (e.g., by pipetting up and down the cells).

According to the present invention, the single cell suspension of human fetal pulmonary cells comprises viable cells. Cell viability may be monitored using any method known in the art, as for example, using a cell viability assay (e.g. MultiTox Multiplex Assay available from Promega), Flow cytometry, Trypan blue, etc.

Typically, the isolated population of fetal pulmonary cells are immediately used for transplantation. However, in situations in which the cells are to be maintained in suspension prior to transplantation, e.g. for 1-12 hours, the cells may be cultured in a culture medium which is capable of supporting their viability. Such a culture medium can be a water-based medium which includes a combination of substances such as salts, nutrients, minerals, vitamins, amino acids, nucleic acids, proteins such as cytokines, growth factors and hormones, all of which are needed for maintaining the isolated population of fetal pulmonary cells in an viable state. For example, a culture medium according to this aspect of the present invention can be a synthetic tissue culture medium such as Ko-DMEM (Gibco-Invitrogen Corporation products, Grand Island, N.Y., USA), DMEM/F12 (Biological Industries, Beit Haemek, Israel), Mab ADCB medium (HyClone, Utah, USA) or DMEM/F12 (Biological Industries, Biet Haemek, Israel) supplemented with the necessary additives. Preferably, all ingredients included in the culture medium of the present invention are substantially pure, with a tissue culture grade.

Cells isolated from the fetal pulmonary tissue may comprise a heterogeneous population of cells.

According to one embodiment, the isolated population of cell suspension comprises progenitor cells. The progenitor cells may comprise, for example, epithelial progenitor cells, mesenchymal progenitor cells, hematopoietic progenitor cells and/or endothelial progenitor cells.

According to one embodiment, the cells comprise a cytokeratin 5+ (CK5+) marker expression.

According to one embodiment, the cells comprise a cytokeratin 5+ (CK5+) and cytokeratin 14+ (CK14+) marker expression.

According to one embodiment, the cells comprise a c-Kit+ CD45− CD34− marker expression.

According to one embodiment, the cells comprise a c-Kit+ CD45− CD34− CD31− CD326− CD271− marker expression.

According to one embodiment, the cells comprise a c-Kit+ CD34+ marker expression.

According to one embodiment, the cells comprise a c-Kit+ CD34+ CD31+ marker expression.

According to one embodiment, the cells comprise a c-Kit+ CD34+ CD326+ marker expression.

According to one embodiment, the cells comprise a CD34+ CD31+ CD14+ CD45+ marker expression.

According to one embodiment, the cells comprise a CD34+ CD31+ CD45− CD105+ marker expression.

According to one embodiment, the cells comprise a nestin+ marker expression.

According to one embodiment, the cells comprise a calcitonin gene related protein+ (CGRP+) marker expression.

According to one embodiment, the cells comprise an alpha smooth muscle actin+ (alpha-SMA+) marker expression.

According to one embodiment, the cells comprise a Vimentin+ marker expression.

According to a specific embodiment, each of the cell populations mentioned hereinabove may be of about 50%, 60%, 70%, 80%, 90% or 100% purification.

Purification of specific cell types may be carried out by any method known to one of skill in the art, as for example, by affinity based purification (e.g. such as by the use of MACS beads, FACS sorter and/or capture ELISA labeling) using specific antibodies which recognize any of the above described cell markers (e.g. CK5, CK14, c-Kit, CD31, CD34, CD45, CD105, CD271, CD326, etc.).

According to an embodiment of the present invention, the isolated population of cell suspension comprises a non-purified mixture of the isolated population of fetal pulmonary cells.

According to another embodiment, the isolated population of cell suspension comprises a cell-type specific population of fetal pulmonary cells (as indicated in further detail above). Isolating such cells may be carried out by any method known to one of skill in the art, as for example, by affinity based purification (e.g. such as by the use of MACS beads, FACS sorter and/or capture ELISA labeling, as mentioned above) or by eradication (e.g. killing) of unwanted cells with specific antibodies targeting same.

It will be appreciated that the cells within the isolated population of cell suspension are capable of regenerating a structural/functional pulmonary tissue, including generation of a chimeric lung. The chimeric lung comprises alveolar, bronchial and/or bronchiolar structures, and/or vascular structures. Furthermore, the structural/functional pulmonary tissue comprises an ability to synthesize surfactant [e.g. clara cell secretory protein (CCSP), aquqporin-5 (AQP-5) and surfactant protein C (sp-C)], detectable by specific cell staining, and/or an ability to transportions (e.g. as indicated by staining for CFTR-cystic fibrosis transmembrane regulator). The cells within the isolated population of cell suspension are further capable of regenerating an epithelial, mesenchymal and/or endothelial tissue (e.g. epithelial, mesenchymal and/or endothelial tissue, as indicated by the formation of a complete chimeric lung tissue comprising all of these components).

Thus, the use of cells isolated from the fetal pulmonary tissue is especially beneficial in situations in which there is a need to regenerate epithelial, mesenchymal and/or endothelial tissue, including pulmonary tissue.

Thus, according to another aspect of the present invention, there is provided a method of regenerating an epithelial, mesenchymal and/or endothelial tissue in a subject in need thereof, the method comprising administering to the subject a therapeutically effective amount of the pharmaceutical composition of some embodiments of the present invention.

According to another aspect of the present invention, there is provided a method of treating a disease or condition in which regeneration of epithelial, mesenchymal and/or endothelial tissue is beneficial in a subject in need thereof, the method comprising administering to the subject a therapeutically effective amount of the pharmaceutical composition of some embodiments of the present invention.

According to another aspect of the present invention, there is provided a method of treating a pulmonary disorder or injury in a subject in need thereof, the method comprising administering to the subject a therapeutically effective amount of the pharmaceutical composition of some embodiments of the present invention.

As used herein, the term "epithelial tissue" refers to a tissue which lines any of the cavities or surfaces of structures throughout the mammalian body. Exemplary epithelial tissues include, but are not limited to, lung tissue, gastrointestinal tract tissue, reproductive organ tissue, urinary tract tissue, renal tissue, skin tissue, ischemic tissue, cardiac tissue, endothelial tissue, circulatory tissue and brain tissue.

As used herein, the term "mesenchymal tissue" refers to a connective tissue in the mammalian body that is derived mostly from mesoderm. Exemplary mesenchymal tissues include, but are not limited to, the connective tissues of the body, the blood and the lymphatic vessels.

As used herein, the term "endothelial tissue" refers to a thin layer of cells that lines the interior surface of blood vessels and lymphatic vessels. Exemplary endothelial tissues include, but are not limited to, lymphatic tissues and circulatory system tissues (e.g. blood vessels).

As used herein, the term "regenerating a tissue" refers to reconstruction of an epithelial, mesenchymal or endothelial tissue such that a functional tissue is formed (i.e. a tissue which functions as a native tissue in the specified region). Thus in some embodiments of the present invention, regenerating refers to at least about 10%, 20%, 30%, 40%, 50%, 60%, 70%, 80%, 90% or 100% increase in epithelial, mesenchymal or endothelial tissue.

Any method known to one of skill in the art may be used to assess regeneration of an epithelial tissue (e.g. pulmonary tissue), mesenchymal tissue (e.g. connective tissue) or endothelial tissue (e.g. blood vessels) as for example, using x-ray, ultrasound, CT, MRI, histological staining of a tissue sample from the epithelial tissue (e.g. by staining for clara cell secretory protein (CCSP), aquqporin-5 and surfactant protein C expression), mesenchymal tissue (e.g. by staining for Vimentin$^+$expression) or endothelial tissues (e.g. by staining for CD31 expression).

As used herein, the terms "subject" or "subject in need thereof" refer to a mammal, preferably a human being, male or female at any age, who suffers from or is predisposed to an epithelial, mesenchymal or endothelial tissue damage or deficiency as a result of a disease, disorder or injury.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "disease or condition in which regeneration of epithelial, mesenchymal and/or endothelial tissue is beneficial" refers to any disease, disorder, condition or to any pathological or undesired condition, state, or syndrome, or to any physical, morphological or physiological abnormality which involves a loss or deficiency in epithelial, mesenchymal and/or endothelial tissue. Typically, such a disease or condition includes a pulmonary disorder, disease or injury; a renal disorder, disease or injury; a hepatic disorder, disease or injury; a gastrointestinal tract disorder, disease or injury; a skin disorder, disease or injury; a vascular disorder, disease or injury; a cardiac disorder, disease or injury; or a brain disorder, disease or injury.

Exemplary diseases or conditions in which regeneration of epithelial tissue is beneficial include, but are not limited to, chronic ulcers, inflammatory bowel disease (IBD), Crohn's disease, ulcerative colitis, Alzheimer's disease, Parkinson's disease, skin burns, skin ulcers, skin wounds, chronic obstructive pulmonary disease (COPD), cystic fibrosis, emphysema, asbestosis, pulmonary fibrosis (e.g. idiopathic pulmonary fibrosis), pulmonary hypertension, lung cancer, sarcoidosis, lung failure, acute lung injury (adult respiratory distress syndrome), congenital diaphragmatic hernia, respiratory distress syndrome of prematurity, chronic lung disease of prematurity (bronchopulmonarydysplasia), surfactant protein B deficiency (e.g. homozygos surfactant protein B deficiency), pulmonary alveolar proteinosis, pulmonary hypoplasia and lung injury corneal degeneration and cancer.

Exemplary diseases or conditions in which regeneration of mesenchymal tissue is beneficial include, but are not limited to, heart diseases or conditions, diabetes, deafness, Crohn's disease, autoimmune disorders, leukemia and lymphoma, cancer (e.g. breast cancer), sickle cell disease, amyotrophic lateral sclerosis and metabolic disorders.

Exemplary diseases or conditions in which regeneration of endothelial tissue is beneficial include, but are not limited to, vascular diseases, ischemia, sickle cell disease, cardiovascular diseases, atherosclerosis, diabetes and autoimmune disorders [e.g. systemic lupus erythematosus (SLE) and the antiphospholipid antibody syndrome (aPS)].

Examples of cancer include, but are not limited to, carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Examples of autoimmune disorders/diseases include, but are not limited to, cardiovascular diseases (e.g. atherosclerosis, thrombosis, myocardial infarction, etc.), rheumatoid diseases (e.g. rheumatoid arthritis and ankylosing spondylitis), glandular diseases (e.g. pancreatic disease, Type I diabetes, thyroid disease, Graves' disease, thyroiditis, etc.), gastrointestinal diseases (e.g. chronic inflammatory intestinal diseases, celiac disease, colitis, ileitis and Crohn's disease), cutaneous diseases (e.g. autoimmune bullous skin diseases, such as, but are not limited to, pemphigus vulgaris, bullous pemphigoid and pemphigus foliaceus), hepatic diseases (e.g. hepatitis, autoimmune chronic active hepatitis, primary biliary cirrhosis and autoimmune hepatitis), neurological diseases (e.g. multiple sclerosis, Alzheimer's disease, myasthenia gravis, neuropathies, motor neuropathies; Guillain-Barre syndrome and autoimmune neuropathies, myasthenia, Lambert-Eaton myasthenic syndrome; paraneoplastic neurological diseases, cerebellar atrophy, paraneoplastic cerebellar atrophy and stiff-man syndrome; non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies; dysimmune neuropathies; acquired neuromyotonia, arthrogryposis multiplex congenita, neuritis, optic neuritis and neurodegenerative diseases), muscular diseases (e.g. myositis, autoimmune myositis, primary Sjogren's syndrome and smooth muscle autoimmune disease), nephric diseases (e.g. nephritis and autoimmune interstitial nephritis), diseases related to reproduction (e.g. repeated fetal loss), connective tissue diseases (e.g. ear diseases, autoimmune ear diseases and autoimmune diseases of the inner ear) and systemic diseases (e.g. systemic lupus erythematosus and systemic sclerosis). As used herein, the term "pulmonary disorder or injury" refers to any disease, disorder, condition or to any pathological or undesired condition, state, or syndrome, or to any physical, morphological or physiological abnormality which involves a loss or deficiency in pulmonary tissue.

Exemplary disease or condition associated with a pulmonary disorder or injury include, but are not limited to, cystic fibrosis, emphysema, asbestosis, chronic obstructive pulmonary disease (COPD), pulmonary fibrosis (e.g. idiopatic pulmonary fibrosis), pulmonary hypertension, lung cancer, sarcoidosis, lung failure, acute lung injury (e.g. adult respiratory distress syndrome), congenital diaphragmatic hernia, respiratory distress syndrome of prematurity, chronic lung disease of prematurity (bronchopulmonarydysplasia), surfactant protein B deficiency (e.g. homozygos surfactant protein B deficiency), pulmonary alveolar proteinosis, pulmonary hypoplasia and lung injury.

Administration of the isolated population of cell suspension to the subject may be effected in numerous ways, depending on various parameters, such as, for example, the type, stage or severity of the disease to be treated, the physical or physiological parameters specific to the individual subject, and/or the desired therapeutic outcome. For example, depending on the application and purpose administration of the isolated population of cell suspension may be effected by a route selected from the group consisting of intratracheal, intrabronchial, intraalveolar, intravenous, intraperitoneal, intranasal, subcutaneous, intramedullary, intrathecal, intraventricular, intracardiac, intramuscular, intraserosal, intramucosal, transmucosal, transnasal, rectal and intestinal.

According to one embodiment, administering is effected by an intravenous route.

Alternatively, administration of the isolated population of cell suspension to the subject may be effected by administration thereof into various suitable anatomical locations so as to be of therapeutic effect. Thus, depending on the application and purpose, the isolated population of fetal pulmonary cells may be administered into a homotopic anatomical location (a normal anatomical location for the organ or tissue type of the cells), or into an ectopic anatomical location (an abnormal anatomical location for the organ or tissue type of the cells).

Accordingly, depending on the application and purpose, the isolated population of fetal pulmonary cells may be advantageously implanted (e.g. transplanted) under the renal capsule, or into the kidney, the testicular fat, the sub cutis, the omentum, the portal vein, the liver, the spleen, the heart cavity, the heart, the chest cavity, the lung, the pancreas, the skin and/or the intra abdominal space.

For example, for treatment of a gastrointestinal disease or condition, the isolated population of cell suspension of the present invention may be administered into the liver, the portal vein, the renal capsule, the sub-cutis, the omentum, the spleen, the intra-abdominal space, the pancreas, the testicular fat and/or an intestinal loop (the subserosa of a U loop of the small intestine). For treatment of a pulmonary disease or condition, the isolated population of cell suspension of the present invention may be administered into the lung, under the renal capsule, the liver, the portal vein, the sub-cutis, the omentum, the spleen, the intra-abdominal space, the pancreas and/or the testicular fat.

The isolated population of fetal pulmonary cells of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the isolated population of cell suspension from a mammalian fetal pulmonary tissue accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient (e.g. pulmonary tissue).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (i.e. isolated population of cell suspension comprising fetal pulmonary cells) effective to prevent, alleviate or ameliorate symptoms of a disorder (e.g., epithelial disease, such as, pulmonary disease or condition) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

An exemplary animal model which may be used to evaluate the therapeutically effective amount of an isolated population of fetal pulmonary cells comprises the murine animal model (e.g. mice), in which lung injury is induced by e.g. intraperitoneal injection of naphthalene (e.g. more than 99% pure) with or without further irradiation (e.g. 40-48 hours after naphthalene administration), as described in detail in the Examples section which follows.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide ample levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to an embodiment, the isolated population of cell suspension comprises at least about $0.5 \times 10^5$, $1 \times 10^5$, $0.5 \times 10^6$, $1 \times 10^6$, $1.5 \times 10^6$, $2 \times 10^6$, $2.5 \times 10^6$, $3 \times 10^6$, $3.5 \times 10^6$, $4 \times 10^6$, $4.5 \times 10^6$, $5 \times 10^6$, $5.5 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $10 \times 10^6$ cells per kilogram body weight of the subject.

According to a specific embodiment, the isolated population of cell suspension comprises at least about $1 \times 10^6$ cells per kilogram body weight of the subject.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Encapsulation techniques are generally classified as microencapsulation, involving small spherical vehicles, and macroencapsulation, involving larger flat-sheet and hollowfiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxycinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 µm. Such microcapsules can be further encapsulated with an additional 2-5 µmof ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 µm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

As mentioned, in order to facilitate engraftment of non-syngeneic cells, the present invention further contemplates treating the subject with an immunosuppresssion regimen prior to, concomitantly with or following administration of the isolated population of cell suspension.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto DW., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

According to one embodiment, the immunosuppressive regimen consists of administering at least one immunosuppressant agent to the subject.

Examples of immunosuppressive agents include, but are not limited to, methotrexate, tacrolimus, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, Copaxone, prednisone, methyl prednisolone, azathioprene, cyclophosphamide and fludarabin, CTLA4-Ig, anti CD40 antibodies, anti CD40 ligand antibodies, anti B7 antibodies, anti CD3 antibodies (for example, anti human CD3 antibody OKT3), mycophenolate mofetil, daclizumab [a humanized (IgG1 Fc) anti-IL2R alpha chain (CD25) antibody], and anti T cell antibodies conjugated to toxins (for example, cholera A chain, or *Pseudomonas* toxin), TNF.alpha. blockers, a biological agent that targets an inflammatory cytokine, and Non-Steroidal Anti-Inflammatory Drug (NSAIDs), including, acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, tramadol, rapamycin (sirolimus) and rapamycin analogs (such as CCI-779, RAD001, AP23573). These agents may be administered individually or in combination.

Depending on the type of cells and the disease or condition to be treated, and in order to facilitate engraftment of the isolated population of fetal pulmonary cells, the method may further advantageously comprise conditioning the subject under sublethal, lethal or supralethal conditions prior to administration of the isolated population of cell suspension.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

According to one embodiment, the conditioning comprises total body irradiation (TBI), total lymphoid irradiation (TLI, i.e. exposure of all lymph nodes, the thymus, and spleen), partial body irradiation (e.g. specific exposure of the lungs, kidney, brain etc.), myeloablative conditioning, co-stimulatory blockade, chemotherapeutic agent and/or antibody immunotherapy.

As illustrated in the Examples section which follows, conditioning a subject using naphthalene induces site-specific ablation of Clara cells in respiratory bronchioles and in broncho-alveolar junctions and thus facilitate engraftment of the isolated population of fetal pulmonary cells. To further effectively eliminate residential lung stem cells (which may proliferate rapidly after naphthalene treatment), subject were further subjected to sublethal TBI (e.g. 6 Gy) prior to administration of the isolated population of fetal pulmonary cells (see Example 2 of the Examples section which follows).

Thus, according to an embodiment of the present invention, the conditioning protocol comprises Naphthalene treatment.

According to one embodiment, Naphthalene treatment is administered to the subject 1-10 days (e.g. 3 days) prior to administration of the isolated population of cell suspension.

According to one embodiment, the conditioning comprises Naphthalene treatment and TBI treatment.

According to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-7.5 Gy.

According to an embodiment, TBI treatment is administered to the subject 1-10 days (e.g. 1-3 days) prior to administration of the isolated population of cell suspension.

According to one embodiment, Naphthalene treatment is administered to the subject 2-10 days (e.g. 3 days) prior to administration of the isolated population of cell suspension and TBI treatment is administered to the subject 40-48 hours thereafter (e.g. 1 day) prior to administration of the isolated population of cell suspension.

According to one embodiment, when partial body irradiation is used exposure is specific to an organ or tissue to be treated (e.g. lungs, kidney, liver, pancreas, brain etc.). In such cases, it is advisable to shield the non-irradiated body organs in order to avoid unwanted organ/tissue damage.

According to one embodiment, the conditioning comprises a chemotherapeutic agent (e.g. myeloablative agents). Exemplary chemotherapeutic agents include, but are not limited to, Busulfan, Myleran, Busulfex, Fludarabine, Melphalan, Dimethyl mileran and Thiotepa and cyclophosphamide. The chemotherapeutic agent/s may be administered to the subject in a single dose or in several doses e.g. 2, 3, 4, 5, 6, 7, 8, 9, 10 or more doses (e.g. daily doses) prior to transplantation.

According to one embodiment, the conditioning comprises an antibody immunotherapy. Exemplary antibodies include, but are not limited to, an anti-CD52 antibody (e.g. Alemtuzumab sold under the brand names of e.g. Campath, MabCampath, Campath-1H and Lemtrada) and an anti-thymocyte globulin (ATG) agent [e.g. Thymoglobulin (rabbit ATG, rATG, available from Genzyme) and Atgam (equine ATG, eATG, available from Pfizer)]. According to one embodiment, the antibody is administered to the subject in a single dose or in several doses e.g. 2, 3, 4, 5, 6, 7, 8, 9, 10 or more doses (e.g. daily doses) prior to transplantation.

According to one embodiment, the conditioning comprises co-stimulatory blockade. Thus, for example, the conditioning may comprise transiently administering to the subject at least one T-cell costimulation inhibitor and at least one CD40 ligand inhibitor, and more preferably may further comprise administering to the subject an inhibitor of T-cell proliferation.

According to one embodiment, the T-cell co-stimulation inhibitor is CTLA4-Ig, the CD40 ligand inhibitor is anti-CD40 ligand antibody, and the inhibitor of T-cell proliferation is rapamycin. Alternately, the T-cell costimulation inhibitor may be an anti-CD40 antibody. Alternately, the T-cell costimulation inhibitor may be an antibody specific for B7-1, B7-2, CD28, anti-LFA-1 and/or anti-LFA3.

Following transplantation of the isolated population of cell suspension into the subject according to the present teachings, it is advisable, according to standard medical practice, to monitor the growth functionality and immuno-compatibility of the transplanted cells according to any one of various standard art techniques. For example, the functionality of regenerated pulmonary tissues may be monitored following transplantation by standard pulmonary function tests (e.g. analysis of functional properties of the developing implants, as indicated by the ability to synthesize surfactant, detectable by staining for surfactant protein C (sp-C) and the ability to transportions, as indicated by staining for CFTR-cystic fibrosis transmembrane regulator).

The isolated population of fetal pulmonary cells described herein may be stored individually or may be comprised in a bank, each population being categorized according to a particular parameter (e.g. HLA type).

Thus, according to still another aspect of the present invention there is provided a cell bank comprising a plurality of cell populations isolated from mammalian fetal pulmonary tissues, wherein the fetal pulmonary tissues are at a developmental stage essentially corresponding to that of a human pulmonary organ/tissue at a gestational stage selected from a range of about 20 to about 22 weeks of gestation, and wherein the plurality of cell populations have been HLA typed to form an allogeneic cell bank, each individually disposed within separate containers.

According to one embodiment, the human pulmonary organ/tissue is at a gestational stage as described in detail hereinabove.

According to an embodiment, the bank doesn't comprise cells from gestational stages other than the above mentioned.

According to an embodiment, the bank doesn't comprise cells from gestational stages other than the above 20-22 weeks of gestation.

According to an embodiment, the bank doesn't comprise cells from tissues other than lung.

According to an embodiment, the bank doesn't comprise cells from post natal or adult tissues.

The mammalian fetal pulmonary cell bank of this aspect of the present invention is a physical collection of one or more mammalian fetal pulmonary cell populations derived from fetuses at a gestational age corresponding to human 20-22 weeks of gestation. Such banks preferably contain more than one sample (i.e., aliquot) of each fetal pulmonary cell population. Harvesting fetal pulmonary cell populations is described hereinabove. The fetal pulmonary cell populations may be derived from various mammalian organisms, as described hereinabove.

The fetal pulmonary cell populations are stored under appropriate conditions (typically by freezing) to keep the cells (e.g. progenitor cells) alive and functioning. According to one embodiment, the fetal pulmonary cell populations are stored as cryopreserved populations. Other preservation methods are described in U.S. Pat. Nos. 5,656,498, 5,004,681, 5,192,553, 5,955,257, and 6,461,645. Methods for banking stem cells are described, for example, in U.S. Patent Application Publication No. 2003/0215942.

According to one embodiment, the fetal pulmonary cell populations stored in the bank are characterized according to predetermined characteristics including, but not limited to, morphological characteristics, differentiation profile, blood type, major histocompatibility complex [human leukocyte antigen (HLA)], disease state of donor, or genotypic information associated or not associated with a disease or condition.

According to one embodiment, the fetal pulmonary cell populations stored in the bank are characterized according to HLA typing.

According to one embodiment, the cell bank further comprises a catalogue which comprises information about the predetermined characteristics (e.g. HLA typed cells) of the fetal pulmonary cell populations.

Cataloguing may constitute creating a centralized record of the characteristics obtained for each cell population, such as, but not limited to, an assembled written record or a computer database with information inputted therein. The fetal pulmonary cell bank facilitates the selection from a plurality of samples of a specific fetal pulmonary cell sample suitable for a researcher's or clinician's needs.

According to yet another aspect of the present invention there is provided a method of isolating mammalian fetal pulmonary progenitor cells, the method comprising: (a) obtaining a mammalian fetal pulmonary tissue, wherein the fetal pulmonary tissue is at a developmental stage essentially corresponding to that of a human pulmonary organ/tissue at a gestational stage selected from a range of about 20 to about 22 weeks of gestation; (b) detecting marker expression on fetal pulmonary tissue cells of a marker selected from the group consisting of CK5, CK14, CD271, CD34, c-Kit, CD326, CD31, and CD45 and a combination of same; and (c) isolating the cells exhibiting the marker expression, thereby isolating the mammalian fetal pulmonary progenitor cells.

According to one embodiment, the isolated population of cells comprises at least two times more CK5+ cells compared to a pulmonary tissue or organ obtained from about 15 or 17 weeks of gestation.

According to one embodiment, the isolated population of cells results in newly formed epithelial cells in small bronchioles of a lung of the subject.

According to one embodiment, the isolated population of cells results in expression of Pneumocyte type 1 cells and/or Pneumocyte type 2 cells in an alveoli of a lung of the subject.

According to one embodiment, the isolated population of cells results in an expression of $CD31^+$ cells in a blood vessel of a lung of the subject.

According to one embodiment, the isolated population of cells results in wider alveolar ducts compared to a pulmonary tissue or organ obtained from about 18 weeks of gestation.

According to one embodiment, the isolated population of cells results in thinner alveolar walls compared to a pulmonary tissue or organ obtained from about 18 weeks of gestation.

According to one embodiment, the isolated population of cells results in more bronchial and bronchiolar structures compared to a pulmonary tissue or organ obtained from about 18 weeks of gestation.

According to one embodiment, the isolated population of cells does not results in formation of cysts compared to a pulmonary tissue or organ obtained from about 15 or 24 weeks of gestation.

According to one embodiment, the isolated population of cells results in positive expression of surfactant protein C (sp-C) and/or CFTR compared to a pulmonary tissue or organ obtained from about 15 or 24 weeks of gestation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Fetal Lung Xenografts
Animals
Animals were maintained under conditions approved by the Institutional Animal Care and Use Committee at the Weizmann Institute. Mice strains used included: NOD-SCID, RAG-/-, Balb- Nude, C57BL/6J (CD45.2) and C57BL/6-Tg(CAG-EGFP)1Osba. All mice were of 6-10 weeks of age. They were kept in small cages (up to five animals in each cage) and fed sterile food and acid water.
Animal Procedures
Transplantation Procedure
Transplantations of the embryonic precursor tissues were performed under general anesthesia (2.5% 2,2,2-tribromoethanol, 97% in PBS, 10 ml/kg administered intraperitoneally) as previously described [Katchman H. et al., Stem Cells. (2008) 26(5):1347-55].
Implantation Under the Kidney Capsule
Host kidney was exposed through a left lateral incision. A 1.5-mm incision was made at the caudal end of the kidney capsule, and donor precursor tissues were grafted under the kidney capsule in fragments 1-2 mm in diameter.
Human fetal lung tissues, ranging from 15 to 24 weeks of gestation, were obtained from legal abortions where written informed consent for use of lung tissue was obtained according to a protocol approved by the Helsinki Ethics Committee. Fetal age was determined based on clinical information and confirmed by fetal foot-length measurements. To ensure that graft tissue was derived from fetal lung, only whole lung lobes were used for preparation of xenograft tissue. Fresh lower airways were cut under sterile conditions into 1-3 $mm^3$ pieces. Surgery was performed on anesthetized immunodeficient mice, and human fetal lung tissue was placed beneath the renal capsule of each mouse (one piece). Xenografts were harvested at different time points after grafting.

For syngeneic transplantation of mouse embryonic lung under the kidney capsule of C57BL mice, lungs from different gestational age embryos (14-17 days of gestation) were harvested and grafted under the kidney capsule in fragments 1-2 mm in diameter. To ensure that graft tissue was derived from fetal lung, only whole lung lobes were used for preparation of graft tissue.

The animals receiving implants were sacrificed at 2-20 weeks after transplantation. Kidneys bearing the transplanted grafts were then removed and fixed in 4% paraformaldehyde or cryopreserved Tissue sections were routinely stained by hematoxylin and eosin (H&E). Assessment of graft differentiation and function was performed by histochemical and immunohistochemical labeling.

Morphometric Analysis
Human embryonic lungs of different gestational ages were frozen in Optimal Cutting Temperature compound (OCT), and cut in cryocut. Consecutive 12 im sections were stained with primary rabbit anti-human CK5 antibody (Abcam), and secondary donkey anti-rabbit Day Light 594 antibody. The areas of interest were quantified using the Image Pro program (Media Cybernetics, Crofton, Md.). At least 3-4 different samples of lungs of the same gestational age were analyzed.

Naphthalene Lung Injury
For lung injury studies, mice were given an intraperitoneal injection of naphthalene (more than 99% pure; Sigma-Aldrich), dissolved in corn oil, 200 mg per kg body weight, 40-48 hours before transplantation].

For "double lung" injury, naphthalene treated animals were further irradiated (40-48 hours after naphthalene administration): C57BL mice were irradiated with 6 Gy TBI; NOD-SCID mice were irradiated with 3-4 Gy TBI.

Lung Single Cell Suspension and Transplantation
Cell Preparation and Injection
Cell suspensions were obtained from enzyme-digested 15-24 week lungs. Briefly, lung digestion was performed by finely mincing tissue with a razor blade in the presence of 0.1% collagenase, 2.4 U/ml dispase (Roche Diagnostics, Indianapolis, Ind.) and 2.5 mM $CaCl_2$ at 37° C. for 1 h. Removal of nonspecific debris was accomplished by sequential filtration through 70- and 40-μm filters.

Following conditioning with naphthalene (NA), TBI, or both, each animal was transplanted with $1 \times 10^6$ GFP-positive embryonic lung cells, injected into the tail vein 4-8 hours following irradiation.

Flow Cytometry
Human (15-24 week) and mouse (14-17 week) embryonic lung derived single cell suspensions, and adult mouse and adult human single cell suspensions were analyzed by polychromatic flow cytometry. All the samples were stained with conjugated antibodies or matching isotype controls according to manufacturer's instructions. Antibodies were from Bioscience, BD, and Biolegend. The complete list of antibodies used in the study is summarized in Table 2, hereinbelow. Data were acquired on an LSRII (BD Biosciences) flow cytometer, and analyzed using Flow Jo software (version 7.6.5).

Immunochistochemistry
Animals were sacrificed at different time points following transplantation; the lungs were inflated with 4% PFA solution and kept for 24 hours, then cryopreserved in 30% sucrose and snap-frozen in isopentane pre-cooled by liquid air, or processed for paraffin embedding. Paraffin blocks were cut in 4 μm sections, and stained after xylene deparaffinization and rehydration as previously described [Hecht G et al., Proc Nat Acad of Sci. (2009) 106(21): 8659]. The summary of antibodies used in the study is depicted in Table 2, hereinbelow. All secondary antibodies were from Jackson Immunoresearch Laboratories.

The images were acquired by Olympus digital camera (DP70), and occasionally processed by Adobe photoshop 7.0. For all immunohistochemical stainings, a negative control was run using the same technique but omitting the primary antibody while adding the labeled secondary antibody.

TABLE 2

A list of the antibodies used in the study

Primary antibodies

Rabbit anti CK antibody (Abcam)
Mouse anti human CK18 antibody (Daco)
Mouse anti human CK14 antibody (Daco)
Mouse anti human MNF (Santa Cruz)
Mouse anti human Ki-67 antibody (Daco)
Mouse anti human nestin antibody (MBL)
Goat anti mouse nestin antibody (Santa Cruz)
Rabbit anti mouse CCSP antibody (Abcam)
Rabbit anti GFP (Abcam)
Chicken anti GFP (Abcam)
Goat anti human CGRP (Santa Cruz)
Chicken anti Thyrosine Hydroxilase Antibody (Abcam)
Rabbit anti surfactant protein C antibody (Santa Cruz)
Rabbit anti CFTR (Abcam)
Rat anti human CD31 antibody (Daco)
Rabbit anti mouse CD31 antibody (Daco)
Mouse anti human CD11c antibody (Daco)
Rabbit anti CD20 antibody (Daco)
Mouse anti CD3 antibody (Daco)
Anti mouse Sca-PE; Anti mouse Sca-FITC antibody (Biolegend)
Anti mouse CD45-APC antibody (Biolegend)
Anti mouse CD31-APC; Anti mouse CD31-PE-Cy7 antibody (Biolegend)
Anti mouse CD326-Percp-Cy5.5 (Biolegend)
Anti mouse CD49f-FITC (Biolegend)
Anti mouse CD24-PE-Cy7 (Biolegend)
Anti mouse CD104-Pacific blue (Biolegend)
Anti mouse CD90-Pacific blue (Biolegend)
Anti mouse CD73-PE (Biolegend)
Anti human CD45-APC-Cy77 (Biolegend)
Anti human CD326-APC (Biolegend)
Anti human CD117-PE (Biolegend)
Anti human CD271-FITC (Biolegend)
Anti human CD31-Pacific blue (Biolegend)
Anti human CD34-Percp (Biolegend)
Anti human CD14-PE (Mylteni)
Anti human CD105-Pacific blue (Mylteni)
Anti human CD2-FITC (BD)
Anti human CD20-PE (BD)
Secondary antibodies Anti-mouse-Daylight 488
Anti-mouse-Daylight 594
Anti-rat-Daylight 488
Anti-rat-Daylight 594
Anti-rat-AMCA
Anti-rabbit-Alexa Fluor 488
Anti-rabbit-Cy5
Anti-rabbit-AMCA
Anti-goat-Alexa Fluor 488
Anti-goat-Rhodamine Red
Anti-goat-AMCA
Anti-chicken-Alexa Fluor 488

(Of note, all the secondary antibodies were purchased from Jackson ImmunoResearch or Abcam)

Two-Photon Microscopy

Before imaging, mice were euthanized, or injected I.V. with blood tracer Quantom dots 655 nano-particles for vascular labeling (Invitrogen—Molecular Probes) and then euthanized. Lungs were excised and put under a glass-covered imaging chamber.

An Ultima™ Multiphoton Microscope (Prairie Technologies Middleton, Wis.) incorporating a pulsed Mai Tai™ Ti-sapphire laser (Newport Corp., CA) was used. The laser was tuned to 850 nm to simultaneously excite EGFP and the blood tracer. A water-immersed 20× (NA 0.95) or 40× objective (NA 0.8) or 10× air objective (NA 0.3) from Olympus was used.

To create a typical Z stack, sections of the lung containing GFP cells were scanned at a depth of approximately 30-150 μm with 3 μm Z-steps. The data were analyzed using Volocity® software (Perkin-Elmer, Coventry, UK).

Micro-CT Imaging

Micro-CT imaging was performed under general anesthesia (2.5% 2,2,2-tribromoethanol, 97% in PBS, 10 ml/kg administered intraperitoneally.

In vivo micro-CT experiments were performed on Tomo-Scope® 30S Duo scanner (CT Imaging, Germany) equipped with two source-detector systems. The operation voltage of both tubes were 40 kV. The integration time of the first and second protocols was 90 ms (360 rotation) and 5 min (360° rotation) and axial images were obtained at an isotropic resolution of 80 μm. The processing of the CT data was analyzed using the ImageJ software.

Statistical Analysis

Differences between groups were evaluated by the Student's t-test. Data are expressed as mean±SD or mean±SEM, as indicated, and were considered statistically significant for p-values≤0.05.

Example 1

Optimal 'Window' for Harvesting Human Embryonic Lung Precursor Tissue

Growth Potential of Human Embryonic Lung Tissues Harvested at Different Gestational Time Points To assess the influence of embryonic stage on growth and differentiation potential, lung embryonic progenitor tissues originating from 15- to 24-week human fetuses were first transplanted under the renal capsule of NOD-SCID mice. Overall, upon examination at 8 weeks post transplant, more than 98% of the grafts from donor tissue of all ages survived and all recovered grafts demonstrated increased size, with no evidence of neoplasia in any of the recovered grafts. Nevertheless, results were distinctly different when similar transplantation was attempted using earlier or later-gestation lungs as donor tissues.

As can be seen in FIG. 1A, tissue harvested at 20-22 weeks, (n=25, 1-3 mm in size) exhibited enhanced growth at 8 weeks after transplantation (reaching a size of 300.7+/−15.2 mm), compared to tissue harvested at 15-19 or 23-24 weeks of gestation (61.6+/−3.5 mm and 10.6+/−2.0 mm, respectively).

To obtain a quantitative evaluation of the different structural attributes in the growing lung implant, shown macroscopically in FIG. 1B, morphometric analysis was employed.

As shown in FIGS. 1C-F, all elements of the respiratory tree, similar in their appearance to adult human lung tissue, were detected in implants growing from week 20-22 tissue. Thus, formation of alveolar ducts with alveoli (FIGS. 1C-F), trachea covered with ciliated epithelium (FIG. 1E), muscular layers and cartilage (FIG. 1E), and alveolar epithelial monolayers (FIG. 1F), were all exhibited by the growing implants.

Likewise, parameters which define functional properties of the developing implants, as indicated by the ability to synthesize surfactant, detectable by staining for surfactant protein C (sp-C) (FIGS. 1G-H), and ability to transportions, as indicated by staining for CFTR-cystic fibrosis transmembrane regulator (FIG. 1I), were clearly expressed. Typically, these functional markers appearing relatively late during the maturation process, coincide with the more differentiated elements expressing cytokeratin 18 (CK 18) and they are not expressed in 20 w tissue prior to transplantation (data not shown).

Surprisingly, and in contrast to the above results, implants originating from tissue harvested at 15 weeks (FIG. 1J-L) or 24 weeks (FIG. 1M-O) developed cysts and were negative for sp-C and CFTR staining (data not shown), while implants originating from 18 week tissue, although exhibiting all the patterns of differentiation and maturation, including staining for sp-C and CFTR (data not shown), were still defective, in that the formed alveolar ducts were narrower, and alveolar walls were thicker (FIG. 1P-R). Taken together, these results suggest that the optimal 'window' for harvesting human embryonic lung tissue for transplantation is between 20-22 weeks of gestation.

Identification of Stem Cell Progenitors and their Niches in Human Embryonic Lung Tissue at Different Gestational Time Points Following the identification of optimal 'window' human embryonic lung tissue for transplantation, the presence of putative stem cells in this 'window' tissue was evaluated compared to tissues harvested at earlier or later gestational time points.

As shown in FIGS. 2A-D, H&E staining revealed that more bronchial and bronchiolar structures are found in tissues harvested at 20-22 weeks compared to tissues harvested at earlier time points. To define potential differences in progenitor levels in these tissues, the presence of the putative progenitor subpopulation of basal epithelial lung cells, previously shown to express cytokeratins 5 (CK5) and 14 (CK14), was examined. These distinct markers are down-regulated upon differentiation, in parallel to expression of the more mature CK8/CK18 positive phenotype.

As can be seen in FIG. 2E, marked frequency of CK5 positive cells was found in the large airways along with expression of CK14 (FIG. 2F), while a somewhat lower abundance was found in the developing alveoli. Furthermore, this immunohistological staining revealed that the CK5+ cells were surrounded by nestin$^+$ cells (FIG. 2G), and some of them exhibited properties of neuroepithelial bodies marked by calcitonin gene related protein (CGRP). As can be seen in FIG. 2H, this innervation was further revealed by staining for neurofilaments (NF), suggesting an architecture of stem cell niches similar to those previously defined for hematopoietic stem cells in the bone marrow, and in adult mouse airways. Furthermore, in line with a very recent report regarding the BM niche, the epithelial CK5$^+$niche also contained alpha-smooth muscle actin positive cells (FIG. 2I and FIGS. 5A-D) and Vimentin$^+$ mesenchymal cells (FIG. 2J).

Importantly, morphometric analysis demonstrated a relative abundance of CK5$^+$ progenitors at the 'window' tissue of 20-22 weeks of gestation, suggesting that the optimal window is likely associated with a higher number of these progenitors. Thus, in the tissue harvested at 20-22 weeks of gestation, the CK5+area was found to represent an average of 14.1%±5.6 of the total lung tissue, compared to 5.26%±1.06 (P=0.0006) or 6.05%±0.18 (P=0.002), in 15 w and 17 w tissues, respectively (FIGS. 2K-O).

Taken together, this "window of opportunity" for harvesting embryonic lung as a source for transplantation can be explained in part by the frequency of CK5 positive epithelial progenitor cells, and their respective niches. To further investigate other putative progenitors in different embryonic tissues, a FACS analysis was used to determine the presence of several phenotypes recently attributed to pluripotential human lung stem cells. In particular, attention was focused on two phenotypes. The first, a rare subpopulation, stained positive for c-kit (CD117) and negative for many differentiation markers including CD34, was described recently by Kajstura et al. mainly in adult lung tissue, but also in embryonic tissue, the authors suggested that these cells represent a multipotent lung stem cell, with self-renewing capacity [Kajstura J. et al., N Engl J. Med. (2011) 364(19): 1795-806; Anversa P. et al., Nat. Med. (2011) 17(9):1038-9] and with regenerative potential for all lung lineages. However, Suzuki et al. maintain that in the embryonic lung, the C-Kit$^+$ cells also express CD34 and are likely endothelial progenitors [Moodley Y. et al., N Engl J. Med. (2011) 365(5):464-6; Suzuki T. et al., American Journal of Respiratory and Critical Care Medicine (2010) 181 (1 Meeting Abstracts): A4898], therefore, the presence of C-Kit$^+$CD34$^+$ cells was also evaluated (FIGS. 2P-Z).

To that end, single cell suspensions obtained from enzymatically treated human embryonic lung tissues, harvested at 16, 18 and 20 weeks of gestation, were analyzed for the expression of several differentiation markers including CD34 (specific for hematopoietic and endothelial progenitors), CD45 (hematopoietic cells), CD31 (marker for endothelial cells), CD117 (c-KIT, to identify early progenitors), CD271 (NGFR, mesenchymal stem cell marker), and CD326 (EPCAM, epithelial differentiation marker).

Strikingly, the non-hematopoietic, CD45 negative population was found to comprise three distinct C-Kit$^+$ progenitor populations, including CD34$^{high}$, CD34$^{intermediate}$, and CD34$^{negative}$ cells (FIGS. 2P-T). While the latter population is compatible with the early pluripotential adult lung stem cells, the other CD34$^+$ cells might be more strongly differentiated towards the endothelial lineage also expressing high levels of CD31 (FIGS. 5A-I).

Interestingly, the C-Kit$^+$ CD34$^{neg}$ subpopulation was clearly more abundant in tissues harvested at 20 weeks (about up to 2-3% of CD34$^{neg}$ population) compared to earlier gestational ages (less than 0.15%) or to adult lung tissue used as a control (less than 0.45%, FIGS. 6A-L). These unique C-Kit$^+$ CD45$^-$CD34$^-$CD271$^-$ cells, which are also negative for CD31 and CD326 (FIGS. 7A-I), in line with Kajstura et al. could also be identified by immunohistology. Thus, as shown in FIGS. 3A-C, these putative progenitors were present at low levels in close proximity to large airways, mainly in perivascular spaces.

Importantly, when lung tissues were analyzed by immunohistological staining for CD117 and CD34, several distinct cell sub-populations were found similar to those found by the FACS analysis. Analysis of a 20 week human lung is shown in FIGS. 4A-K; the majority of CD117$^+$ cells co-expressed CD34 and resided in blood vessels (FIGS. 4A-C) surrounding developing alveoli (FIGS. 4D-G), while the minor CD 117$^+$ single positive cell sub-population were found in close proximity to large blood vessels and large airways (FIG. 4H-K). Similar pattern of CD117+ cell distribution was found in earlier gestational age lung tissues (FIGS. 8A-D), although the total percentage as revealed by FACS was significantly higher in the 20 w tissue (FIGS. 2A-Z). Furthermore, as shown in FIGS. 9A-D, the 20 week embryonic tissues also exhibit early and late endothelial progenitor cells (EPC) which may have a unique role in lung microvascular repair. Thus, this tissue was also found to exhibit the presence of two distinct CD34+ CD31+ subpopulations. The first one identified by positive staining for CD14 and CD45, whereas the second subpopulation is CD45⁻CD105+, in line with previous studies suggesting the presence of these two major types of EPCs in human peripheral blood [Yoder M C et al., Blood. (2007) 109(5): 1801-9]. The former one termed 'early EPCs' are characterized by early growth in vitro, CD34/CD31/CD14 positivity, the inability to form tubes in a Matrigel tube forming assay, and high levels of cytokine secretion. The other type of EPC, termed 'late outgrowth EPCs', 'outgrowth endothelial cells (OECs)' or 'endothelial colony forming cells (ECFC)' is characterized by CD31 and CD105 positivity, lack of CD45 and CD14, and the unique ability to spontaneously form human blood vessels when implanted in a gel into immunodeficient mice, integrating with murine vessels of the systemic circulation.

Example 2

Proof of Concept in Mouse Models for the Regenerative Potential of 'Window' Embryonic Lung Transplants Optimal 'Window' for Harvesting Mouse Embryonic Lung Precursor Tissue for Transplantation In order to assess the curative potential of embryonic lung derived tissue in appropriate mouse models, the optimal "window" for harvesting mouse embryonic lung for transplantation was initially defined, as for its human counterpart. Thus, mouse lung embryonic tissue was harvested at different gestational time points (E14-E17), implanted under the kidney capsule of syngeneic mice, and 8 weeks after transplantation, the implants were assessed for the presence of lung parenchyma, bronchial and alveolar structures, as well as for unwanted presence of fibrosis and cysts.

Figure 10F:
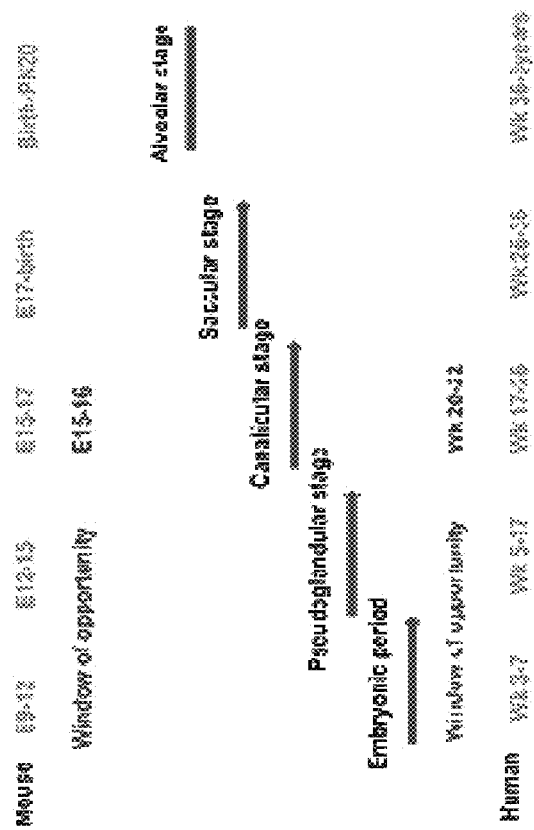
FIG. 10F depicts a schematic representation of parallel stages in mouse and human lung development. The "optimal window" for transplantation is within the canalicular stage of development.
Figures 10D, 10E:
FIGS. 10A-E depict characterization of embryonic tissues before and after implantation under the renal capsule of syngeneic mice.
Figures 10A, 10B, 10C:
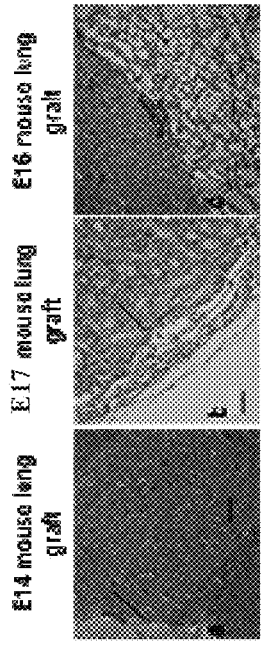

As can be seen in FIGS. 10A-E, twelve weeks after sub-capsular renal transplantation, E14 and E17 lung tissue resulted in formation of cystic and fibrotic tissue (FIGS. 10A-B), while E15-E16 mouse embryonic lung exhibited marked potential to further differentiate and to reach the alveolar stage (FIG. 10C-E). Thus, similar to human lung tissue, the canalicular stage of lung development offers the optimal window for harvest of tissue for transplantation (FIG. 10F). Also, similarly to the human 'window' tissue, the E16 lung tissue exhibited no alveoli (FIG. 11A); CK-5 positive cells were abundant in large airways, and numerous neuroepithelial bodies were found within the entire sample, which stained positively for CGRP and were localized in niches (FIG. 11B) similarly to bone marrow and adult mouse lung (FIGS. 12A-F). Likewise, CCSP-positive cells were found in the regions of large airways, which were rich in nestin-positive cells (FIG. 11C), suggestive of stem cell niches, and were surrounded by alpha-SMA positive cells (FIG. 11D).

In addition, similarly to their human counterparts, the E15-E16 tissue was enriched with putative progenitors compared to early or later gestational tissues, as shown by FACS analysis of CD45⁻CD31⁻EpCAM⁺CD24⁺CD49f⁺CD104⁺ cells, recently established as putative lung progenitors in adult mouse lung [McQualter J L et al., Proceedings of the National Academy of Sciences. (2010) 107(4):1414]. Thus, as can be seen in FIGS. 3E-Y, depicting representative FACS analysis of E13, E14, E15 and E16 single cell suspensions, markedly higher levels of CD45⁻CD31⁻ EpCAM⁺ CD24⁺ CD49f⁺CD104⁺ cells were found in E15 and E16 lung tissue (0.062%±0.007 and 0.073%±0.005, respectively) compared to the level in E13 and E14 tissue (0.002±0.00057% and 0.012±0.0057%, respectively).

Transplantation of E16 Mouse Embryonic Lung Cells for the Treatment of Lung Injury Considering that E15-16 tissues exhibit marked growth and differentiation potential upon transplantation, this 'window' tissue was further evaluated in a mouse model for lung injury.

To that end, these cells were initially evaluated in a model based on injury induction with naphthalene, as previously described [Stripp B et al, American Journal of Physiology-Lung Cellular and Molecular Physiology. (1995) 269(6): 791]. This lung injury model mimics lung diseases caused by mild epithelial injury, detectable by changes in the expression of pulmonary Clara cells.

The particular anatomical localization of Clara cells in respiratory bronchioles and in broncho-alveolar junctions enabled to accurately localize the site of injury after naphthalene exposure, and to test the ability of a single cell suspension of embryonic "window" cells to colonize and restore the injured epithelial layer in syngeneic recipients.

Two days following naphthalene administration, recipient C57BL mice were infused with 1×10⁶ E16 lung cells, derived from GFP-positive pregnant mice. Subsequently, the lungs of the treated animals were histologically assessed at different time points for the presence of GFP-positive cells. These initial experiments (not shown) revealed that ablation of Clara cells by naphthalene was transient and could not enable significant engraftment and development of donor-derived Clara cells. Thus, the present inventors hypothesized that a more aggressive conditioning regimen, more effectively ablating resident stem cell proliferation, might be required for the assessment of the regenerative capacity of donor cells, as commonly found in studies measuring chimerism induction following bone marrow transplantation.

To test this hypothesis, 40 hours following naphthalene injury, animals were additionally treated with sublethal TBI (6 Gy) so as to eliminate resident lung stem cells, which are potentially induced to proliferate by prior naphthalene treatment.

After 1 day, the mice received E16 lung cells, and were followed for engraftment and development of donor-derived cells in their lungs by immunohistological staining coupled with morphometric analysis, as well as by 2-photon microscopy.

As shown in FIGS. 13A-C, GFP positive 'patches', indicating engraftment of donor-derived cells in the recipient lungs were markedly enhanced at 30 days post transplant, in mice conditioned with both naphthalene and 6 Gy TBI (FIG. 13C) compared to TBI alone (FIG. 13A), or naphthalene alone (FIG. 13B). This marked impact of conditioning on lung chimerism level is demonstrated quantitatively in FIG. 13D, depicting morphometric analysis of the GFP patches found in three independent experiments comprising a total of nine mice in each group. Thus, while 55 foci/mm³ donor-derived foci were found in mice conditioned with naphthalene and 6 Gy TBY, only 10-12 foci/mm³, and 2-3 foci/mm³, were found in mice conditioned with naphthalene or TBI alone, respectively.

Immunohistological examination of mice exhibiting chimeric lungs, further revealed the level of integration into functional elements in the recipients lungs. As shown in FIG. 14A, lumens of the large airways of untreated control mice clearly exhibited the presence of CCSP⁺ Clara cells, and these cells underwent ablation and peeling immediately after the conditioning (FIG. 14B). However, mice transplanted after the conditioning of choice, exhibited at day 30 post transplant, formation of a new epithelial layer, and engrafted GFP+ cells were found in the bronchial lumens. These donor derived GFP+ cells incorporated into the host bronchial and alveolar airways, and were vascularized, as shown by staining for V-cadherin (FIG. 14C); They also expressed CCSP (FIGS. 14D-F), and were positive for Sp-c (FIGS. 14G-I) and CFTR expression (FIGS. 14J-L), suggesting their ability to produce surfactant and engage in ion transport. As expected, these specific functional markers were exhibited differentially by the engrafted GFP+ cells according to their location. Thus, in large airways, the cells were positive for CCSP, and in alveoli, the engrafted cells were positive for sp-C, but all the cells were found to express CFTR, which is of particular significance for potential correction of cystic fibrosis (CF).

Interestingly, when tested at later time points post transplant, the initial foci were clearly growing in size and thereby occupying a larger proportion of the engrafted lungs. This was further demonstrated by 2-photon microscopy, enabling direct view of the lungs immediately after sacrifice, with or without intravital co-staining of blood vessels with red Quantum dots for fluorescent vascular labeling (data not shown). As can be seen in FIGS. 15A-C, while a moderate engraftment of the lung by donor type cells was found at 6 weeks post transplant, with a predominant integration of transplanted GFP+ cells in the broncho-alveolar and vascular structures (FIGS. 15A-B), further progression of donor type cells occupying almost third of the lung tissue, was found at 4 months post transplant (FIG. 15C).

Furthermore, immunohistological assessment of these chimeric lungs at 16 weeks after transplantation, revealed the full integration of donor derived cells, in the gas exchange surface at the interface of blood vessels and in alveolar epithelial structures (FIGS. 16A-L). Thus, GFP+ cells were found by triple staining with CD31 and anti-pan-cytokeratin antibodies to be incorporated into vascular and epithelial compartments of transplanted lungs, without signs of scarring or fibrosis (FIGS. 16A-D and FIGS. 17A-E). Likewise, the AQP (FIGS. 16E-H) and SP-C (FIGS. 16I-L) staining revealed incorporation of donor derived cells in the gas-exchange surface of type I and type II alveocytes, respectively.

Collectively, these results strongly suggest that embryonic lung cells harvested from 'window' tissue could offer a novel cell source for lung tissue repair. Furthermore, it is anticipated that therapy with such cells could be more effective if combined with sub-lethal conditioning, although this might be less critical in clinical situations at which host lung progenitors are markedly ablated by the ongoing injury.

Transplantation of a Single Cell Suspension Derived from 20-22 w Human Embryonic Lung into NOD-SCID Mice, Following Lung Injury Induction with Naphthalene and TBI To investigate the ability of 'window' human embryonic lung cells to integrate into injured lungs, a lung injury model was established in immunodeficient SCID mice. Considering that NOD-SCID mice are more sensitive to TBI, 3.0 GY TBI were used instead of 6.0 Gy TBI used in the studies with mouse donor-tissue, described above. Furthermore, as a replacement for the genetic GFP labeling, immunohistology with mouse and human specific antibodies was used to distinguish between host and donor epithelial, endothelial, and mesenchymal cells.

Thus, while infusion of $1\times10^6$ cells harvested after enzymatic digestion of 20 w human embryonic lung cells into NOD-SCID mice, conditioned with NA alone, did not result in any appreciable level of engraftment (data not shown), marked chimerism was attained following infusion of the same number of cells into NOD-SCID mice conditioned with naphthalene and subsequent treatment with 3.0 Gy TBI (FIGS. 18A-I and 19A-F).

In an initial short term experiment, a human embryonic (20 w) lung-derived single cell suspension was stained with the tracking fluorescent dye, 5-(and -6)(((4-Chloromethyl) Benzoyl)Amino)Tetramethylrhodamine) (CMTMR), and the cells were infused into conditioned NOD-SCID mice. When examined 2 weeks later, engrafted human cells could be visualized within distinct patches in the lung of the recipient mice (FIG. 24A), similar to GFP+ patches found in the syngeneic transplantation model (FIG. 24B). As the CMTMR staining is transient, a second set of experiments was carried out to distinguish the human and mouse cells at later time points following transplantation, by immunohistological staining using an anti-mouse MHC antibody not cross reactive with control human tissue (FIGS. 24C-E), and the anti-human cytokeratin MNF 116 antibody (staining human epithelial cells), not cross reactive with control mouse tissue, as verified by double staining in FIGS. 24F-H.

Importantly, at 6 weeks post transplant, double staining with these antibodies clearly revealed a significant level of chimerism. As can be seen in FIGS. 18A-C, showing low magnification of mouse bronchi, double staining with the mouse and human markers clearly demonstrates incorporation of human derived cells into the lung structure, and this can be further appreciated under high magnification of two different fields (FIGS. 18D-F and 18G-I, respectively).

In a third set of experiments, human embryonic lung cells harvested at 20 w were transplanted into NOD-SCID treated with NA and slightly higher TBI (4 Gy).

The mouse lungs were stained 7 weeks after transplantation with additional distinguishing anti-mouse and anti-human markers. Thus, mouse anti-human cytokeratin MNF 116 antibody (staining human epithelial cells), mouse anti-human V9 (staining vimentin 9, typical of stromal cells), and mouse anti-human CD31 (staining endothelial cells) were mixed together and placed on the tissue section; sections were then incubated with a second anti-mouse IgG antibody labeled with Daylight 488 (green). FIGS. 19A and 19D show the selective staining by this antibody cocktail of human tissues in the bronchial structure of mouse lung. Cells of mouse origin in the mouse lung were stained with Banderia lectin The latter is known to bind to α-Gal moiety expressed on mouse epithelial and endothelial cells, and as can be seen, it is not cross reactive with the human tissue when monitored alone (FIGS. 19B and 19E) or in conjunction with MNF staining FIGS. 19C and 19F). Furthermore, using similar markers, marked chimerism could also be detected in the alveoli of transplanted mice (FIGS. 20A-F). Importantly, the human lung cells derived from transplantation of human embryonic cells were also found to exhibit several important functional markers.

As can be seen in FIGS. 21A-C, double staining of the human cells marked in green by the cocktail described above (FIG. 21A) together with a general marker of cytokeratin, resulted in staining of all epithelial cells of both mouse and human origin (FIG. 21B), illustrating distinct epithelial cells within the human cell population in the engrafted lung (FIG. 21C). Likewise, human cells positive for aquaporin-5 (AQP-5), typical of type I alveocytes (FIGS. 22A-C) and human cells positive for surfactant protein C(SP-C) characteristic of type II alveocytes (FIGS. 23A-F) were clearly distinguished within the chimeric lungs of transplanted animals at 7 weeks following transplantation.

Thus, human derived lung cells are not only incorporated into the injured mouse lung but also express AQP-5, required to perform gas-exchange, or SP—C, indicating production of surfactant by the alveoli.

Treatment with Embryonic Lung Derived Stem Cells is not Associated with Teratoma Development One of the most controversial issues in embryonic stem cell transplantation, which limits their clinical application, is the potential tumorigenicity of the transplanted tissues. In previous studies in which the present inventors attempted to define the optimal 'window' for different pig embryonic precursor tissues, results showed that beyond E28, none of the tested tissues exhibit any risk for teratoma formation [Eventov-Friedman S et al., Proceedings of the National Academy of Sciences. (2005) 102(8):2928]. Thus, considering that embryonic lungs develop late in embryogenesis, and that, accordingly, the 'window' of choice for mouse, pig or human embryonic lung tissue represents a relatively late stage of gestation, the risk for teratoma induction associated with such precursor tissues is likely very low. However, to further verify this important issue, a detailed histological analysis was performed of the transplanted mice (n=30) up to 12 months following transplantation; no evidence was found of any tumors in the transplanted lung tissue. Furthermore, long term follow up of transplanted mice by lung micro-CT (resolution of 80 µm) did not reveal any suspected space-occupying lesion in these mice. A summary of these results with representative images is demonstrated in FIGS. 25A-D.

Discussion

The present results illustrate that mouse or human lung embryonic tissue, obtained at the canalicular stage, can offer an optimal source for tissue replacement by transplantation. Furthermore, it was proposed that human embryonic lung, rich in early progenitors, resembles in its attributes tissues of the bone marrow and cord blood, whose use for transplantation in hematopoietic diseases has dramatically increased over the past decade. The 'window' embryonic tissues, which exhibited optimal growth and differentiation upon implantation into syngeneic or SCID mice, are significantly enriched for various epithelial, mesenchymal, and endothelial progenitors, compared to tissue from earlier or later gestational time points. Moreover, detailed analysis of these early progenitors in their respective embryonic tissues, revealed that epithelial progenitors reside in specific niches, similar to those described extensively for hematopoietic stem cell niches in the bone marrow. Thus, the present results documented, in proximity to putative lung progenitor cells, the assembly of endothelial cells, nestin-positive cells, and mesenchymal cells, which are also typically innervated, as found by positive staining for CGRP and neurofilaments. These results are consistent with studies indicating the potential existence of stem cell niches in the adult mouse lung [Engelhardt J F. American journal of respiratory cell and molecular biology. (2001) 24(6): 649-52].

In addition to defining the optimal window for use of fetal tissue in transplantation, correlating with the appearance of human embryonic lung progenitor niches, the present study also sheds light on an ongoing debate regarding the phenotype of human lung progenitors. Thus, while Kajstura et al. [Kajstura et al. 2011, supra] described a small population of c-kit$^+$ cells that are negative for all other markers and reside in discrete perivascular areas close to large airway structures, the present inventors found in developing alveoli, another c-kit$^+$ cell population, which resides in blood vessels, in close proximity to CK5$^+$ progenitors, expressing both CD34 and CD31 antigens, as suggested by Suzuki et al. (Suzuki et al 2010, supra). Thus, the 'window' lung embryonic tissue, characterized here, contains both putative c-kit positive progenitor populations. The close proximity and potential interaction of c-kit positive cells with CK5$^+$ epithelial progenitors is consistent with the recent suggestion that c-kit triggering is crucial for normal development and maintenance of alveolar structures [Lindsey J Y et al., American Journal of Respiratory and Critical Care Medicine. (2011) 183 (1 MeetingAbstracts): A2445].

Importantly, the "optimal canalicular window" tissues exhibit the highest level of all types of progenitors relative to lung tissues from earlier developmental stages; thus, the present inventors hypothesized that intravenous transplantation of the unfractionated cell mixture, similarly to the methodology used in bone marrow transplantation, could be the preferred approach. Indeed, transplantation of a single cell suspension of E15-E16 mouse lung or 20-22 w human lung tissue demonstrated the remarkable regenerative capacity of these cells following lung injury induced by combining naphthalene and 6.0 Gy sub-lethal TBI. Critically, this level of conditioning prior to transplantation was necessary to establish chimerism when host lung progenitors were present at significant levels, as found after injury induction with naphthalene. Similar observation was made recently by Duchesneau et al. [Duchesneau P et al., Molecular Therapy. (2010) 18(10): 1830-6] who demonstrated that the engraftment of bone marrow derived cells in lung structures can be markedly enhanced by intensification of the conditioning using the myeloablative agent busulfan in addition to naphthalene. Clearly, this requirement for conditioning might vary in its intensity in different clinical situations, depending on the level of lung injury to host progenitors affected by the pathological process.

Taken together, the present results revealed robust engraftment in different compartments of the host lung and formation of the entire respiratory unit including the following elements: a) Newly formed epithelial cells in small bronchioles, as manifested by GFP$^+$CCSP$^+$ cells. b) Pneumocyte type 1 cells (GFP$^+$AQP-5$^+$), important for the gas-exchange surface within the alveoli. c) Pneumocyte type 2 cells (GFP$^+$ Sp-C$^+$), important for surfactant production in the alveoli. d) Robust presence of GFP$^+$ CD31$^+$ cells in the vasculature. In addition, the engrafted tissue exhibits, along with respiratory elements, expression of CFTR required for ion transport, especially critical for CF patients.

This rather dramatic engraftment following "double injury", as opposed to conditioning with each agent alone, might be explained by competition between host and donor progenitors for their respective niches. Reynolds et al. [Reynolds S D et al., American Journal of Physiology-Lung Cellular and Molecular Physiology. (2004) 287(6): L1256-65] demonstrated that elimination of the CCSP-expressing cell population by naphthalene, results in secondary alveolar inflammation, edema, and depletion of the alveolar type II cell population. Thus, selective airway injury can serve as the inciting injury in diseases characterized by severely compromised alveolar function. Furthermore, Volscaert et al. [Volckaert T et al., J Clin Invest. (2011) 121(10:4409] demonstrated that the Wnt/Fgf10 embryonic signaling cascade is reactivated in mature parabronchial smooth muscle cells (PSMCs) after naphthalene-induced injury, in a manner that activates Notch signaling and subsequent epithelial to mesenchymal transition; this finding indicates that activation of this embryonic pathway could probably serve as a trigger for effective incorporation of the embryonic lung-derived tissue in the different lung compartments. Likewise, radiation-induced lung injury was shown to induce break-down of the blood-alveolus barrier and microcirculation dysfunction, and could thereby enable the dominance of donor-derived endothelial cells (45-47).

Regardless of the mechanism involved, the marked engraftment in the mouse model of donor derived cells attained in both bronchiolar and alveolar structures is striking. This chimerism, which increases over time, can likely be attributed to the multiple donor progenitors in the implanted embryonic lung tissue, enabling progeny of early self-renewing pluripotential stem cells to gradually replace host or donor cells derived from later precursors.

Similar lung integration and development was also observed when testing human lung progenitors in NOD-SCID mice, although in this system, the potential loss of cross-talk with mouse cytokines might reduce engraftment. Thus, in three sets of experiments, the present results illustrated that donor-derived human cells incorporate into both bronchiolar and alveolar structures, exhibiting similar features to those described above for syngeneic embryonic mouse lung cells.

Further studies are required to define optimal immune suppression protocols that will enable successful transplantation in allogeneic recipients. In general, the early embryonic stage might render the implanted donor tissue less immunogenic; however, embryonic tissue transplants cannot evade the indirect pathway of rejection. Nevertheless, this challenge can be addressed by protocols including agents inducing co-stimulatory blockade. Alternatively, the marked level of hematopoietic progenitors (unpublished results) in the embryonic lung tissue might result in hematopoietic chimerism that could induce central tolerance towards donor-derived lung cells after transplantation. In addition, the possibility of cryopreserving single cell suspensions of 20-22 w lung tissue, which could markedly enhance transplant availability, might also enable to establish banks of HLA typed donors as for cord blood, and thereby could potentially reduce the immune suppression requirements.

Finally, the present 'window' mouse embryonic tissue exhibited no risk of teratoma when followed for prolonged time periods after transplantation, by high resolution (80 μm) micro-CT as well as by pathological examination at the end of the follow-up period.

In summary, the present results demonstrate for the first time that the canalicular stage of gestation offers an optimal 'window' for harvesting mouse and human embryonic lung precursor tissue for regenerative transplantation. This tissue, which is free of teratoma risk, is highly enriched for several progenitor types that were identified by immunohistology in their respective niches, similarly to HSCs in the bone marrow. Marked engraftment, differentiation, and robust incorporation of these progenitors into injured lungs, can be provided by infusion of a single cell suspension prepared by enzymatic digestion of the embryonic lung tissue. As in bone marrow transplantation, induction of lung chimerism is dependent on some form of conditioning, so as to reduce competition with host-type endogenous precursors. While various attempts to isolate pluripotential stem cells from adult lungs and to expand these cells in culture for the purpose of regenerative transplantation have been advocated, the present results demonstrate that embryonic lung tissue harvested at 20-22 weeks of gestation could potentially offer a more simple alternative modality for lung repair.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a pulmonary disorder or injury in a subject in need thereof, the method comprising administering to the subject a therapeutically effective amount of a cell suspension from a mammalian fetal pulmonary tissue, wherein said cell suspension comprises a heterogeneous population of cells comprising epithelial progenitor cells, mesenchymal progenitor cells and/or endothelial progenitor cells, and wherein said fetal pulmonary tissue is at a developmental stage corresponding to that of a human pulmonary organ/tissue at a gestational stage selected from a range of 20 to 22 weeks of gestation, and wherein said administering is effected by an intravenous route, thereby treating the pulmonary disorder or injury.

2. The method of claim 1, wherein said subject is a human subject.

3. The method of claim 1, wherein said cell suspension is non-syngeneic with the subject.

4. The method of claim 3, wherein said cell suspension is allogeneic or xenogeneic with the subject.

5. The method of claim 1, wherein said pulmonary disorder or injury is selected from the group consisting of cystic fibrosis, emphysema, asbestosis, chronic obstructive pulmonary disease (COPD), pulmonary fibrosis, idiopathic pulmonary fibrosis, pulmonary hypertension, lung cancer, sarcoidosis, acute lung injury (adult respiratory distress syndrome), respiratory distress syndrome of prematurity, chronic lung disease of prematurity (bronchopulmonary dysplasia), surfactant protein B deficiency, congenital diaphragmatic hernia, pulmonary alveolar proteinosis, pulmonary hypoplasia and lung injury.

6. The method of claim 1, wherein said gestational stage is 20 to 21 weeks of gestation.

7. The method of claim 1, wherein said gestational stage is 21 to 22 weeks of gestation.

8. The method of claim 1, wherein said mammalian fetal pulmonary tissue is a human tissue.

9. The method of claim 1, wherein said cells comprise a cytokeratin 5+ (CK5+) marker expression.

10. The method of claim 1, wherein said cells comprise a cytokeratin 5+ (CK5+) and cytokeratin 14+ (CK14+) marker expression.

11. The method of claim 1, wherein said cells comprise a c-Kit+ CD45− CD34− CD31− CD326− CD271− marker expression.

12. The method of claim 1, wherein said cells comprise a c-Kit+ CD34+ CD31+ marker expression.

13. The method of claim 1, wherein said cells comprise a c-Kit+ CD34+ CD326+ marker expression.

14. The method of claim 1, wherein said cells comprise a CD34+ CD31+ CD14+ CD45+ marker expression.

15. The method of claim 1, wherein said cells comprise a CD34+ CD31+ CD45− CD105+ marker expression.

16. The method of claim 1, wherein said cells comprise a nestin+ and/or a calcitonin gene related protein+ (CGRP+) marker expression.

17. The method of claim 1, wherein said cells comprise an alpha smooth muscle actin+ (alpha-SMA+) and/or a Vimentin+ marker expression.

18. The method of claim 1, wherein said cells are capable of regenerating a structural/functional pulmonary tissue.

19. The method of claim 18, wherein said structural/functional pulmonary tissue comprises generation of a chimeric lung and/or an ability to perform gas-exchange and/or an ability to synthesize surfactant and/or an ability to transport ions.

20. The method of claim 1, wherein said cells are CFTR expressing epithelial cells.

21. The method of claim 1, wherein said cell suspension comprises viable cells.

22. The method of claim 1, further comprising conditioning the subject under sublethal, lethal or supralethal conditioning protocol prior to said administering.

23. The method of claim 22, wherein said conditioning comprises naphthalene treatment.

24. The method of claim 23, wherein said conditioning further comprises total body irradiation (TBI) or partial body irradiation.

* * * * *